United States Patent
Sadow et al.

(10) Patent No.: US 9,856,337 B2
(45) Date of Patent: Jan. 2, 2018

(54) POLYMERIZATION CATALYSTS

(71) Applicants: Iowa State University Research Foundation, Inc., Ames, IA (US); Kumho Petrochemical, Seoul (KR)

(72) Inventors: Aaron David Sadow, Ames, IA (US); Gwanghoon Kwag, Daejeon (KR); Hanbaek Lee, Daejeon (KR); Aradhana Pindwal, Ames, IA (US); Bradley M. Schmidt, Ames, IA (US)

(73) Assignees: Iowa State University Research Foundation, Inc., Ames, IA (US); Kumho Petrochemical, Seoul (KR)

( * ) Notice: Subject to any disclaimer, the term of this patent is extended or adjusted under 35 U.S.C. 154(b) by 0 days.

(21) Appl. No.: 15/081,285

(22) Filed: Mar. 25, 2016

(65) Prior Publication Data
US 2017/0275402 A1  Sep. 28, 2017

(51) Int. Cl.
   *C08F 136/06* (2006.01)
   *C07F 7/08* (2006.01)

(52) U.S. Cl.
   CPC ............ *C08F 136/06* (2013.01); *C07F 7/082* (2013.01)

(58) Field of Classification Search
   CPC .............................. C08F 136/06; C07F 7/082
   See application file for complete search history.

(56) References Cited

U.S. PATENT DOCUMENTS 6,136,931 A   10/2000   Jang et al.

OTHER PUBLICATIONS

Yan et al., "Intermolecular β-Hydrogen Abstraction in Ytterbium, Calcium, and Potassium Tris-(dimethylsilyl)methyl Compounds," Organometallics 2013, 32, 1300-1316.*
Yan et al., "A Tris(alkyl)yttrium Compound Containing Six β-agostic Si—H Interactions," Chem. Commun. 656-658 (2009).
Zhu et al., "Mixed Oxazoline-Cyclopentadienyl Supported Rare Earth Compounds," Presentation at RERC (Jun. 2014).
Aaron D. Sadow, "Organometallic Chemistry at Reactive Ligands' Periphery," Presentation at ETH Zurich (Jul. 2014).
Pindwal et al., "Hydridoborates From β-Hydrogen Abstraction and Comparisons Between Rare Earth and Transition—Metals in Hydroamination," Presentation at LBNL (Sep. 2014).
Maiwald et al., "Highly Active Single-Site Catalysts for the 1,4-Cis Polymerization of Butadiene from Allylneodymium (III) Chlorides and Trialkylaluminums—A Contribution to the Activation of Tris(allyl)neodymium(III) and the Further Elucidation of the Structure-Activity Relationship," Macromol. Chem. Phys. 203:1029-1039 (2002).
Arndt et al, "Homogeneous Ethylene-Polymerization Catalysts based on Alkyl Cations of the Rare-Earth Metals: Are Dicationic Mono(alkyl) Complexes the Active Species?" Agnew. Chem. Int. Ed. 42:5075-5079 (2003).

(Continued)

*Primary Examiner* — Catherine S Branch
(74) *Attorney, Agent, or Firm* — LeClairRyan, a Professional Corporation

(57) ABSTRACT

The present invention relates to processes for polymerizing unsaturated hydrocarbon monomers. The present invention also relates to a precatalyst having the structure of Formula (I):

$$M\{C(SiHAlk_2)_3\}_3 \quad (I),$$

and to a catalyst comprising the structure of Formula (II):

$$MC(SiHAlk_2)_3X_2 \quad (II),$$

and methods for preparation thereof.

62 Claims, 2 Drawing Sheets

(56) References Cited

OTHER PUBLICATIONS

Schmidt and Sadow, "New Butadiene Polymerization Catalysts and Polybutadiene Functionalization," Presentation at Iowa State University, Mar. 30, 2015.
Aaron D. Sadow "Organometallic Chemistry at Reactive Ligands' Periphery," Presentation at Dow (Feb. 2014).
Yan, "Synthesis of Main Group, Rare-Earth, and d0 Metal Complexes Containing Beta-Hydrogen," Iowa State University, Thesis (publication date was in Jun. 21, 2013).

* cited by examiner

POLYMERIZATION CATALYSTS

FIELD OF THE INVENTION

The present invention relates to polymerization catalysts.

BACKGROUND OF THE INVENTION

Homoleptic organometallic compounds, which contain only one type of ligand bonded to a metal center (Zimmermann et al., *Chem. Rev.* 110:6194-6259 (2010); Edelmann et al., *Chem. Rev.* 102:1851-1896 (2002); Harder, S., *Organometallics* 21:3782-3787 (2002); Tsuboyama et al.; *J. Am. Chem. Soc.* 125:12971-12979 (2003); Wayda et al., *J. Am. Chem. Soc.* 100:7119-7121 (1978); Kruse, W., *J. Organomet. Chem.*, 42:C39 (1972); Zucchini et al., *J. Organomet. Chem.* 26:357-372 (1971); Kleinhenz et al., *Chem. Eur. J.*, 4:1687-1691 (1998)) have value in synthetic chemistry as catalysts (Watson et al., *Acc. Chem. Res.* 18:51-56 (1985); Kawaoka et al., *Organometallics*, 22:4630-4632 (2003); Barrett et al., *Proc. R. Soc. A.* 466:927-963 (2010)), as well-defined starting materials for single-site grafting onto supports for catalysis (Copéret et al., *Angew. Chem. Int. Ed.* 42:156-181 (2003); Quignard et al., *J. Chem. Soc. Chem. Commun.* 1589-1590 (1991); Quignard et al., *Inorg. Chem.*, 31:928-930 (1992); J. Amor Nait Ajjou et al., *Organometallics*, 16:86-92 (1997)), as precursors for materials in chemical vapor deposition or other thermal decompositions processes (Valet et al., *Chem Mater.* 13:2135-2143 (2001); Edelmann, F. T., *Chem. Soc. Rev.* 38:2253-2268 (2009)), and for combination with a range of ancillary ligands as an entry-point into reactive organometallic compounds (Trifonov et al., *Organometallics* 20:4869-4874 (2001)). New homoleptic organometallics, thus, can lead to new possibilities in synthesis and catalysis.

Studies of homoleptic rare earth tris(alkyl) starting materials have typically focused on β-hydrogen-free alkyl ligands, namely $CH_2SiMe_3$ (Lappert et al., *J. Chem. Soc. Chem. Commun.* 126 (1973); Atwood et al., *J. Chem. Soc. Chem. Commun.* 140-142 (1978); Schumann et al., *Anorg. Allg. Chem.* 628:2422-2426 (2002)), $CH(SiMe_3)_2$ (Hitchcock et al., *J. Chem. Soc. Chem. Commun.* 1007-1009 (1988)), and $CH_2C_6R_5$ (Wooles et al., *Dalton Trans.* 39:500-510 (2010); Bambirra et al., *Organometallics* 25:3454-3462 (2006); Huang et al., *Organometallics* 32:1379-1386 (2013); Bambirra et al., *Organometallics* 26:1014-1023 (2007)). Applications of homoleptic trivalent compounds containing these ligands, particularly those of the abundant light lanthanides (La, Ce, Pr, Nd), are limited by their thermal lability, challenging multistep syntheses, the formation of salt adducts, or the difficulty to exclude THF from the metal center's coordination sphere. For example, lanthanide tris (benzyl) compounds and their substituted derivatives are limited by the thermal lability of $La(CH_2Ph)_3THF_3$ or $Ce(CH_2Ph)_3THF_3$ at room temperature. Ligand design strategies have sought to overcome these difficulties.

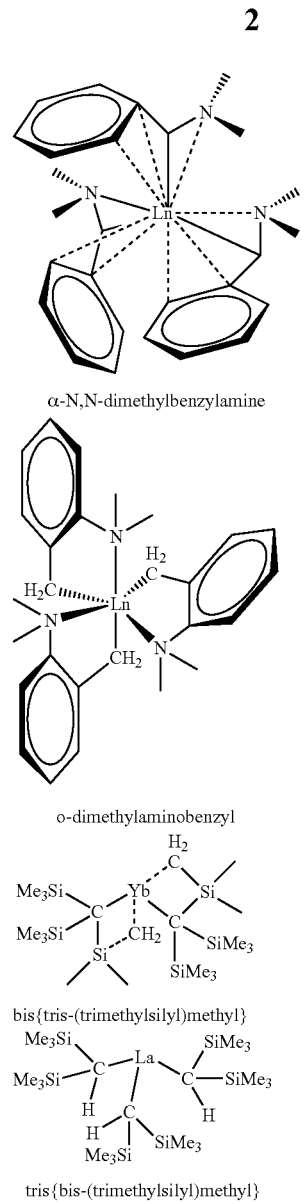

α-N,N-dimethylbenzylamine o-dimethylaminobenzyl bis{tris-(trimethylsilyl)methyl} tris{bis-(trimethylsilyl)methyl}

For example, α-metalated N,N-dimethylbenzylamine lanthanide complexes are persistent at room temperature (Behrle et al., *Organometallics* 30:3915-3918 (2011)). Chelating ortho-dimethylaminobenzyl ligands also give stabilized organolanthanide complexes presumably due to intramolecular coordination (Harder, S., *Organometallics* 24:373-379 (2005)). The bulky alkyl ligand —$C(SiMe_3)_3$, provides homoleptic isolable, donor-solvent free compounds but is restricted to divalent Ln (II) compounds (Eaborn et al., *J. Am. Chem. Soc.* 116:12071-12072 (1994)). Interestingly, non-classical Ln···Me-Si interactions were observed in $Yb\{C(SiMe_3)_3\}_2$ (Eaborn et al., *J. Am. Chem. Soc.* 116: 12071-12072 (1994)) and $La\{CH(SiMe_3)_2\}_3$ (Hitchcock et al., *J. Chem. Soc. Chem. Commun.* 1007-1009 (1988)). In addition, both of these donor-free homoleptic rare earth alkyls adopt solid-state structures that are distorted with respect to VSEPR predictions. $Yb\{C(SiMe_3)_3\}_2$ is bent (C—Yb—C 137°), and $La\{CH(SiMe_3)_2\}_3$ is pyramidal ($\Sigma_{CLaC}$=330°), rather than pyramidal. The significant steric profile is the key to the persistence of these compounds.

The choice of alkyl ligand, however, may not need to be limited to the β-hydrogen-free hydrocarbyl groups. For example, [Ln'Bu₄]⁻ and Cp₂Lu'Bu(THF) are isolable and eliminate isobutylene under only relatively forcing conditions (Schumann et al., *Organometallics* 3:69-74 (1984); Schumann et al., *J. Organomet. Chem.* 306:215-225 (1986); Noh et al., *Polyhedron* 26:3865-3870 (2007); Evans et al., *J. Am. Chem. Soc.* 104:2015-2017 (1982)). In catalysis, particularly ethylene polymerization, ultra-high molecular weight products are obtained from rare earth catalysts, and presumably the long polymer chains are accessible partly because β-hydrogen elimination is slow (Kempe, R., *Chem. Eur. J.* 13:2764-2773 (2007)). In such a scenario, the presence of β-hydrogen may stabilize reactive alkyl groups, as in Cp*₂ScEt and other agostic compounds (Scherer et al., *Angew. Chem. Int. Ed.* 43:1782-1806 (2004), Burger et al., *J. Am. Chem. Soc.* 112:1566-1577 (1990)). Moreover, valuable aspects of metal-ligand bonding and reactivity is ignored in the absence of studies of β-hydrogen containing complexes.

An alternative means for stabilizing metal centers in homoleptic compounds, utilized mainly for amides, involves the β-silicon and β-hydrogen containing ligands such as tetramethyldisilazide —N(SiHMe₂)₂ and tert-butyl dimethylsilazide —N(tBu(SiHMe₂) ligands (Rees Jr. et al., *Angew. Chem. Int. Ed. Eng.* 35:419-422 (1996)). Tetramethyldisilazide has been widely studied in d⁰ and f-element chemistry (Crozier et al., *Chem. Commun.* 49:87-89 (2013); Bienfait et al., *Dalton Trans.* 43:17324-17332 (2014); Anwander et al., *J. Chem. Soc. Dalton Trans.* 847-858 (1998)). Early metal and rare earth silazides containing β-Si—H often form agostic-type structures evident from low energy Si—H vibrations and deviation from Ln-N—Si angles within a given silylamide ligand (Crozier et al., *Chem. Commun.* 49:87-89 (2013); Bienfait et al., *Dalton Trans.* 43:17324-17332 (2014)). Ansa-lanthanidocene compounds containing N(SiHMe₂)₂ ligand exhibit an unusual β Si—H diagostic interactions (Eppinger et al., *J. Am. Chem. Soc.* 122:3080-3096 (2000)). Despite the rich chemistry of tetramethyldisilazido rare earth complexes, the chemistry of rare earth metals with β-SiH containing alkyl remains unexplored.

The chemistry explored thus far for ligands containing β-SiH groups is limited to the silazide. Previously, the synthesis of a β-Si—H containing tris(alkyl)yttrium complex Y{C(SiHMe₂)₃}₃ (Yan et al., *Chem. Commun.* 656-658 (2009)) and bisalkyls M{C(SiHMe₂)₃}₂THF₂ (M=Ca, Yb) (Yan et al., *J. Am. Chem. Soc.* 131:15110-15111 (2009)) was demonstrated. These complexes contained non-classical β Si—H-M interactions, but they did not undergo β-H elimination upon thermolysis to 100° C. even though the metal center was (at least formally) coordinatively unsaturated. However, M{C(SiHMe₂)₃}₂THF₂ (M=Ca, Yb) reacted via β-hydrogen abstraction with Lewis acid.

The present invention is directed to overcoming these and other deficiencies in the art.

SUMMARY OF THE INVENTION

One aspect of the present invention relates to a precatalyst having the structure of Formula (I):

$$M\{C(SiHAlk_2)_3\}_3 \qquad (I),$$

wherein
M is a lanthanide or a transition metal; and
Alk is $C_{1-6}$ alkyl,
wherein if Alk is Me, then M is not Y, La, Ce, or Pr.

Another aspect of the present invention relates to a catalyst comprising the structure of Formula (II):

$$MC(SiHAlk_2)_3X_2 \qquad (II),$$

wherein
M is a lanthanide or a transition metal;
Alk is $C_{1-6}$ alkyl;
X is halide, bis(oxazolinato), carboxylate, acetyl acetonate, amidate, alkoxide, amide, BR₄, AlR₄, or alkyl aluminoxane;
R is independently selected at each occurrence thereof from the group consisting of H, $C_6F_5$, phenyl, and $C_{1-6}$ alkyl; and
wherein if Alk is Me, then M is not Y, La, Ce, or Pr.

Yet another aspect of the present invention relates to a process for preparation of a catalyst. This process includes providing a precatalyst having the structure of Formula (I):

$$M\{C(SiHAlk_2)_3\}_3 \qquad (I),$$

wherein
M is a lanthanide or a transition metal; and
Alk is $C_{1-6}$ alkyl;
wherein if Alk is Me, then M is not Y, La, Ce, or Pr;
providing a Lewis acid or a halide source; and forming the catalyst by reacting the precatalyst having the structure of Formula (I) with the Lewis acid or the halide source.

Another aspect of the present invention relates to a process for preparation of a precatalyst having the structure of Formula (I):

$$M\{C(SiHAlk_2)_3\}_3 \qquad (I),$$

wherein
M is a lanthanide or a transition metal; and
Alk is $C_{1-6}$ alkyl;
wherein if Alk is Me, then M is not Y, La, Ce, or Pr.

Yet another aspect of the present invention relates to a process for polymerizing unsaturated hydrocarbon monomers. This process includes providing unsaturated hydrocarbon monomers; providing a catalyst comprising the structure of Formula (II):

$$MC(SiHAlk_2)_3X_2 \qquad (II),$$

wherein
M is a lanthanide or a transition metal;
Alk is $C_{1-6}$ alkyl;
X is halide, bis(oxazolinato), carboxylate, acetyl acetonate, amidate, alkoxide, amide, BR₄, AlR₄, or alkyl aluminoxane;
R is independently selected at each occurrence thereof from the group consisting of H, $C_6F_5$, phenyl, and $C_{1-6}$ alkyl; and
wherein if Alk is Me, then M is not Y, La, Ce, or Pr; and
polymerizing the unsaturated hydrocarbon monomers in the presence of the catalyst under conditions effective to produce a polymer.

Another aspect of the present invention relates to a process for polymerizing unsaturated hydrocarbon monomers. This process includes providing unsaturated hydrocarbon monomers; providing a catalyst, wherein the catalyst is prepared by the process comprising:
providing a precatalyst having the structure of Formula (I):

$$M\{C(SiHAlk_2)_3\}_3 \qquad (I),$$

wherein
M is a lanthanide or a transition metal; and
Alk is $C_{1-6}$ alkyl;
reacting the precatalyst of Formula (I) under conditions effective to produce the catalyst; and polymerizing the unsaturated hydrocarbon monomers in the presence of the catalyst under conditions effective to produce polymer.

Thermally stable homoleptic rare earth tris(alkyl) complexes $Nd\{C(SiHMe_2)_3\}_3$ were synthesized through salt metathesis reactions of lanthanide triiodides and 3 equiv. of $KC(SiHMe_2)_3$. The isolated, recrystallized product does not contain THF or the KI byproduct in the final product, as determined by single crystal X-ray diffraction studies, NMR spectroscopy, and elemental analysis. Such studies of the complexes revealed pseudo-$C_3$-symmetric tris(alkyl) molecules containing two non-classical Ln—H—Si interactions per alkyl ligand, thereby generating six such interactions in one molecule. Infrared and $^1$HNMR spectroscopic assignments were further supported by preparation of deuterated analogues $Nd\{C(SiDMe_2)_3\}_3$. These organometallic compounds persisted in solution and the solid state up to 80° C. without formation of $HC(SiHMe_2)_3$ or the β-hydrogen elimination product $\{Me_2Si—C(SiHMe_2)_2\}_2$. Reactions of $Nd\{C(SiHMe_2)_3\}_3$ with one and two equiv. of $B(C_6F_5)_3$ resulted in intermolecular β-hydrogen abstraction yielding $Nd\{C(SiHMe_2)_3\}_2HB(C_6F_5)_3$ and $NdC(SiHMe_2)_3\{HB(C_6F_5)_3\}_2$, respectively. The latter compound's structure was determined by single crystal x-ray diffraction, and the rendered thermal ellipsoid plot is shown in FIG. 2.

The present invention relates to the synthesis of new base-free homoleptic trivalent neodymium alkyl complexes. Their reactions with the Lewis acid $B(C_6F_5)_3$ resulted in abstraction of the hydride from the SiH and generation of zwitterion species, which were found to be highly active catalysts for the polymerization of butadiene.

DETAILED DESCRIPTION OF THE INVENTION

Figure 1:
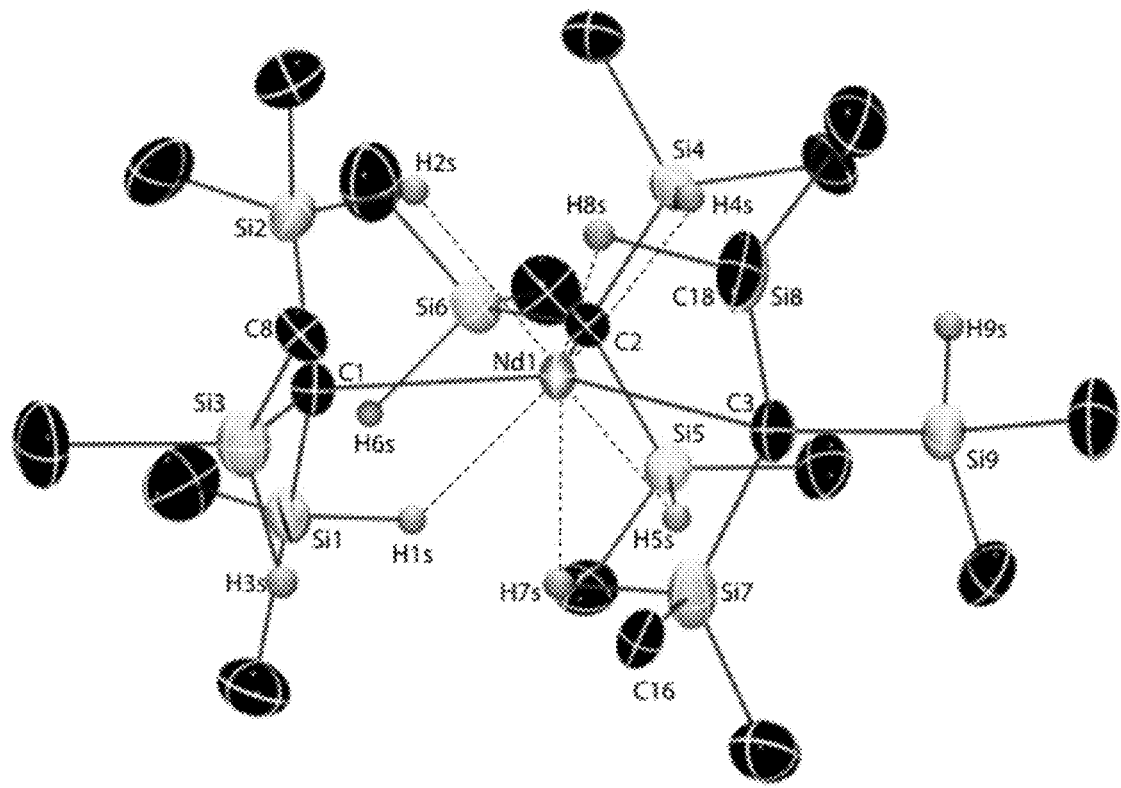
FIG. 1 shows rendered thermal ellipsoid plot showing a side-view of $Nd\{C(SiHMe_2)_3\}_3$ (1d). Ellipsoids were plotted at 50% probability, with the exception of $C^8$, C16, and C18 which were plotted at 25% probability for clarity. Hydrogen atoms bonded to silicon were located objectively in the Fourier difference map, and these were included in the figure. All other H atoms and a co-crystallized benzene molecule were not included for clarity. Significant interatomic distances (Å): Nd1-C1, 2.623(2); Nd1-C8, 2.623(2); Nd1-C15, 2.632(3); Nd1-Si1, 3.1349(9); Nd1-Si2, 3.1727(8); Nd1-Si4, 3.152(1); Nd1-Si5, 3.1435(8); Nd1-Si4, 3.1456(9); Nd1-Si8, 3.1672(7); C1-Si1, 1.830(3); C1-Si3, 1.848(3). Significant interatomic angles)(°): C1-Nd1-C2, 119.04(8); C1-Nd1-C3, 121.01(8); C2-Nd1-C3, 119.88(8); Nd1-C1-Si1, 87.6(1); Nd1-C1-Si2, 89.1(1); Nd1-C1-Si3, 128.5(1); Nd1-C2-Si4, 88.2(1); Nd1-C2-Si5, 87.9(1); Nd1-C2-Si6, 129.9(1); Nd1-C3-Si7, 87.9(1); Nd1-C3-Si8, 88.6(1); Nd1-C3-Si9, 123.5(1).
Figure 2:
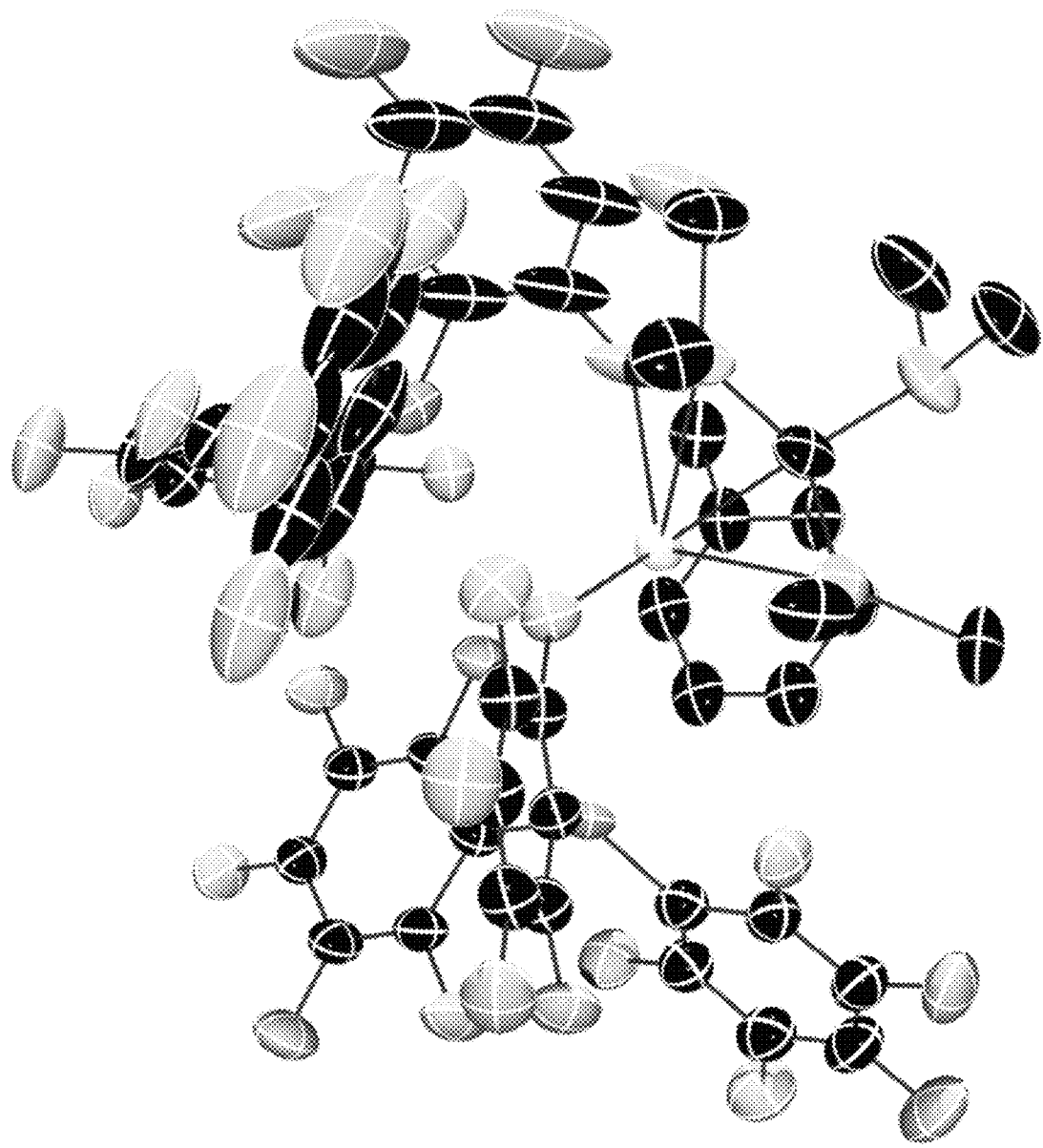
FIG. 2 shows ORTEP diagram of $NdC(SiHMe_2)_3\{HB(C_6F_5)_3\}_2$. Ellipsoids were plotted at 50% probability. Hydrogen atoms bonded to silicon were located objectively in the Fourier difference map. Significant interatomic distances (Å): Nd1-C1, 2.512(11); Nd1-F24, 2.857(6); Nd1-F30, 2.614(6); Nd1-F60, 2.600(7); Nd1-Si1, 3.135(3); Nd1-Si2, 3.101(4); C1-Si1, 1.844(1); C1-Si2, 1.839(1); C1-Si3, 1.870(1). Significant interatomic angles)(°: Nd1-C1-Si1, 90.7(5); Nd1-C1-Si2, 89.6(5); Nd1-C1-Si3, 132.8(6); Si1-C1-Si2, 119.4(7); Si1-C1-Si3, 112.9(6); Si2-C1-Si3, 110.3(7).

One aspect of the present invention relates to a precatalyst having the structure of Formula (I):

  (I), wherein

M is a lanthanide or a transition metal; and

Alk is $C_{1-6}$ alkyl, wherein if Alk is Me, then M is not Y, La, Ce, or Pr.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "lanthanide" or "lanthanide metal atom" refers to the element with atomic numbers 57 to 71. Lanthanides include La, Ce, Pr, Nd, Pm, Sm, Eu, Gd, Tb, Dy, Ho, Er, Tm, Yb, and Lu.

The term "transition metal" refers to an element whose atom has an incomplete d sub-shell, or which can give rise to cations with an incomplete d sub-shell. Transition metals include Sc, Ti, V, Cr, Mn, Fe, Co, Ni, Cu, Y, Zr, Nb, Mo, Tc, Ru, Rh, Pd, Ag, Cd, La, Hf, Ta, W, Re, Os, Ir, Pt, Au, Hg, Ac, Rf, and Ha.

The term "rare earth metal" refers to Y, Sc, and lanthanides. Rare earth metals include Sc, Y, La, Ce, Pr, Nd, Pm, Sm, Eu, Gd, Tb, Dy, Ho, Er, Tm, Yb, and Lu.

The term "alkyl" means an aliphatic hydrocarbon group which may be straight or branched having about 1 to about 30 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "halide" refers to a halogen atom bearing a negative charge.

The term "halogen" means fluoro, chloro, bromo, or iodo.

The term "bis(oxazolinato)" or "BOX" refers to compounds containing two oxazoline rings. Exemplary bis(oxazolinato) ligands are shown below.

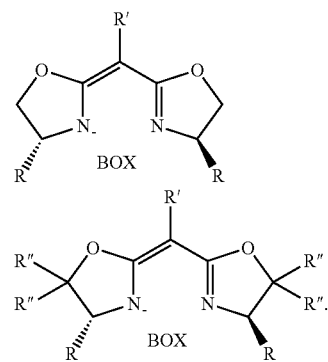

The term "alkyl aluminate" refers to compounds represented by the formula $[Al[O_m(R^1O)_nR^2_o]_n]^-$, wherein $R^1O$ is alkyloxide; $R^2$ is alkyl; the sum of m/2+n+o is 4; and n is 1 to 4.

The term "carboxylate" refers to a conjugate base of a carboxylic acid, $RCOO^-$ (where R is the organic substituent).

The term "acetyl acetonate" refers to the enol form of acetylacetone.

The term "amidate" refers to a carboximate of the type $RCONR'^-$, as the conjugate base of an amide RCONHR' (where R and R' are organic substituents).

The term "alkoxide" refers to the conjugate base of an alcohol, RO⁻ (where R is the organic substituent).

The term "amide" refers to a conjugate base of ammonia (the anion $H_2N^-$) or of an organic amine (an anion $R_2N^-$).

The term "phenyl" means a phenyl group as shown below:

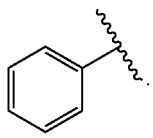 [SMILES: *c1ccccc1]

One embodiment relates to the precatalyst of the present invention where M is a rare earth metal. Another embodiment relates to the precatalyst of the present invention where M is Nd.

In one embodiment, the precatalyst has the structure of Formula (Ia):

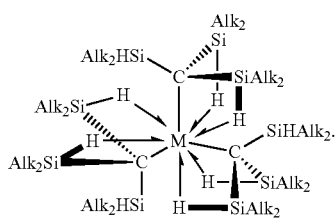

(Ia)

In another embodiment, the precatalyst has the structure of Formula (Ib):

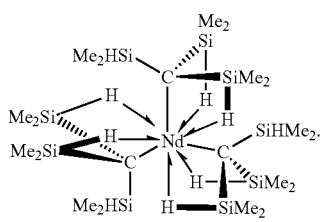

(Ib)

Another aspect of the present invention relates to a catalyst comprising the structure of Formula (II):

MC(SiHAlk₂)₃X₂      (II), wherein
M is a lanthanide or a transition metal;
Alk is $C_{1-6}$ alkyl;
X is halide, bis(oxazolinato), carboxylate, acetyl acetonate, amidate, alkoxide, amide, $BR_4$, $AlR_4$, or alkyl aluminoxane;
R is independently selected at each occurrence thereof from the group consisting of H, $C_6F_5$, phenyl, and $C_{1-6}$ alkyl.

One embodiment relates to the catalyst of the present invention where M is a rare earth metal. Another embodiment relates to the catalyst of the present invention where M is Nd.

Another embodiment relates to the catalyst of the present invention where X is F, Cl, Br, I, $O_2CR^1$, methylaluminoxane (MAO), or $[Ph_3C][B(C_6F_5)_4]$, and where $R^1$ is $C_{1-12}$ alkyl.

In one embodiment, the catalyst comprises the structure of Formula (IIa):

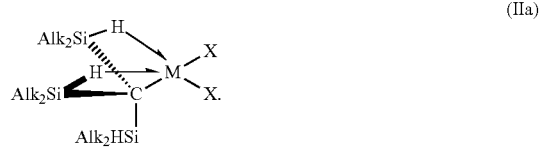

(IIa)

In another embodiment, the catalyst comprises the structure of Formula (IIb):

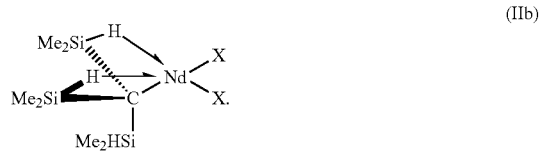

(IIb)

Catalysts of formulae II, IIa, and IIb can be in a monomeric or oligomeric form.

When catalyst of formulae II, IIa, or IIb is present in its monomeric form, it's structure can be represented by formulae II, IIa, or IIb, respectively.

When catalyst of formulae II, IIa, or IIb is present in its oligomeric form, it's structure essentially comprises the repetition of a single constitutional unit (i.e. the molecule of formulae II, IIa, or IIb) with all units connected identically in a directional sense. In one embodiment, oligomeric form of a catalyst of formula II can be represented as follows:

[MC(SiHAlk₂)₃X₂]ₙ, wherein n is 2-8.
In another embodiment, oligomeric form of a catalyst of formula IIa can have a following structure:

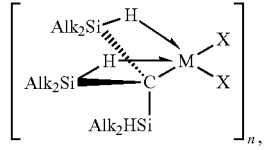

wherein n is 2-8.
In another embodiment, oligomeric form of a catalyst of formula IIb can have a following structure:

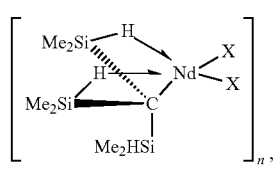

wherein n is 2-8.
In one embodiment, the catalyst having the structure of Formula (II) is supported by an inert carrier. A preferred inert carrier is a porous solid selected from the group consisting of talc, a sheet silicate, an inorganic oxide, and a finely divided polymer powder.

Suitable inorganic oxides are oxides of elements from any of Groups 2-5 and 13-16. Examples of preferred supports include SiO$_2$, aluminum oxide, and also mixed oxides of the elements Ca, Al, Si, Mg, or Ti and also corresponding oxide mixtures, Mg halides, styrene/divinylbenzene copolymers, polyethylene or polypropylene.

Another aspect of the present invention relates to a process for preparation of a catalyst. This process includes providing a precatalyst having the structure of Formula (I):

 (I), as fully described above.

The catalyst of the present invention can be prepared by reacting precatalyst having the structure of Formula (I), M{C(SiHAlk$_2$)$_3$}$_3$, with a Lewis acid or a halide source in a suitable solvent. The use of a non-polar solvent is preferred. In one embodiment, the reaction is carried out at a room temperature. Alternatively, this reaction can be carried out at an elevated temperature. However, room temperature is preferred. The reaction can be carried out in an inert atmosphere or under ambient conditions for 10 min to 24 hours, preferably, for 0.5-2 hours. The molar ratio of the precatalyst to the Lewis acid or a halide source is 1:1 to 1:10, preferably 1:2.

One embodiment relates to the process of the present invention where the catalyst is formed with a Lewis acid. Lewis acid is selected from the group consisting of [Ph$_3$C][B(C$_6$F$_5$)$_4$], B(C$_6$F$_5$)$_3$, Ph$_3$B, PhB(C$_6$H$_5$)$_2$, methylaluminoxane (MAO), modified methylaluminoxane (MMAO), ethylaluminoxane, propylaluminoxane, isopropylaluminoxane, butylauminoxane, isobutylaluminoxane, pentylaluminoxane, neopentylaluminoxane, hexylaluminoxane, octylaluminoxane, 2-ethylhexylaluminoxane, cylcohexylaluminoxane, 1-methylcyclopentylaluminoxane, phenylaluminoxane, 2,6-dimethylphenylaluminoxane, ethylaluminum sesquichloride, diisobutylaluminum chloride, diethylaluminum chloride, ethylaluminum dichloride, ethylaluminum sesquichloride, isobutylaluminum dichloride, dimethylaluminum chloride, isobutylaluminum dichloride, diethylaluminum iodide, diethylaluminum chloride, diisopropylaluminum chloride, diisobutylaluminum chloride, dioctylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenylbutylaluminum chloride, phenylisobutylaluminum chloride, phenyloctylaluminum chloride, p-tolylethylaluminum chloride, p-tolylpropylaluminum chloride, p-tolylisopropylaluminum chloride, p-tolylbutylaluminum chloride, p-tolylisobutylaluminum chloride, p-tolyloctyl aluminum chloride, benzylethylaluminum chloride, benzylpropylaluminum chloride, benzylisopropylaluminum chloride, benzylbutylaluminum chloride, benzylisobutylaluminum chloride, benzyloctylaluminum chloride, propylaluminum dichloride, isopropylaluminum dichloride, butylaluminum dichloride, isobutylaluminum dichloride, and octylaluminum dichloride. In one embodiment, Lewis acid is an alkylaluminum halide.

Another embodiment relates to the process of the present invention where the catalyst is formed with a halide source. The halide source can be Ph$_3$C-Hal, N-chlorosuccinimide, [Alk$_3$NH][Hal], or an electrophilic chlorine source, where Hal is halogen and each Alk is independently selected in each occurrence thereof from C$_{1-6}$ alkyl.

The term "electrophilic chlorine source" refers to an electron-deficient chlorine, generally positively charged (e.g., Cl$^+$), but also possibly a halogen radical (Cl$^-$). In some embodiments, a catalyst comprising an electrophilic chlorine provides a source of Cl$^+$ ions. Exemplary electrophilic chlorine sources include N-chlorosuccinimide (NCS), Cl$_2$, ICl, chloramine-T, and hexachloroquinone.

A further embodiment relates to the process of the present invention further comprising:

providing a first intermediate compound having the structure of Formula (III):

 (III), wherein n is 1 to 9; and forming the precatalyst from the first intermediate compound.

The precatalyst of the present invention can be prepared by reacting MI$_3$THF$_n$ with M$^1$C(SiHAlk$_2$)$_3$ in a protic solvent. A preferred solvent is benzene. In one embodiment, reaction is carried out at room temperature. Alternatively, this reaction can be carried out at an elevated temperature. However, room temperature is preferred. The reaction can be carried out under an inert atmosphere or under ambient conditions. The reaction can be carried out for 1 to 24 hours, preferably, for 10-18 hours, most preferably, 12 hours.

Another embodiment relates to the process of the present invention as described above, wherein said forming the precatalyst is carried out by reacting the first intermediate compound with a compound having the structure of Formula (IV):

 (IV), wherein
M$_1$ is a metal;
under conditions effective to produce the precatalyst.

Yet another embodiment relates to the process of the present invention where M$_1$ is K and Alk is Me.

A further embodiment relates to a catalyst prepared by the process of the present invention.

In another embodiment, the catalyst is supported by an inert carrier.

Another embodiment relates to the process of the present invention where the catalyst comprises a structure of Formula (II):

 (II), wherein
X is halide, bis(oxazolinato), carboxylate, acetyl acetonate, amidate, alkoxide, amide, BR$_4$, AlR$_4$, or alkyl aluminoxane; and
R is independently selected at each occurrence thereof from the group consisting of H, C$_6$F$_5$, phenyl, and C$_{1-6}$ alkyl.

Yet another embodiment relates to the process of the present invention where X is F, Cl, Br, I, O$_2$CR$^1$, methylaluminoxane (MAO), or [Ph$_3$C][B(C$_6$F$_5$)$_4$], and wherein R$^1$ is C$_{1-12}$ alkyl.

A further embodiment relates to the process of the present invention where the catalyst comprises the structure of Formula (IIa):

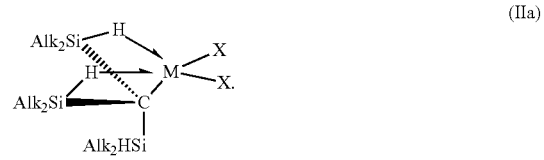

(IIa)

Another embodiment relates to the process of the present invention where the catalyst comprises the structure of Formula (IIb):

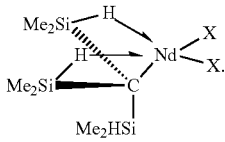 (IIb)

Another aspect of the present invention relates to a process for preparation of a precatalyst having the structure of Formula (I):

 (I), wherein
M is a lanthanide or a transition metal; and
Alk is $C_{1-6}$ alkyl;
wherein if Alk is Me, then M is not Y, La, Ce, or Pr.
This process includes providing a first intermediate compound having the structure of Formula (III):

 (III), wherein n is 1 to 9 and
forming the precatalyst from the first intermediate compound of Formula (III).

One embodiment relates to the process of the present invention wherein said forming the precatalyst comprises:
reacting the first intermediate compound with a compound having the structure of Formula (IV):

 (IV), wherein $M_1$ is a metal;
under conditions effective to produce the precatalyst.

Another embodiment relates to the process of the present invention where the precatalyst has the structure of Formula (Ia):

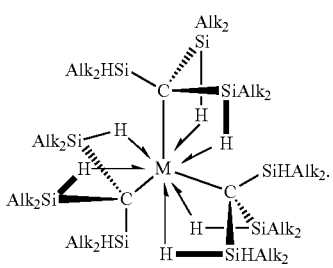 (Ia)

Yet another embodiment relates to the process of the present invention where the precatalyst has the structure of Formula (Ib):

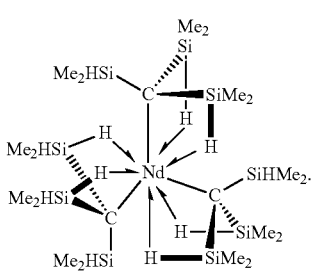 (Ib)

Another aspect of the present invention relates to a process for polymerizing unsaturated hydrocarbon monomers. This process includes providing unsaturated hydrocarbon monomers; providing a catalyst comprising the structure of Formula (II):

 (II), wherein
M is a lanthanide or a transition metal;
Alk is $C_{1-6}$ alkyl;
X is halide, bis(oxazolinato), carboxylate, acetyl acetonate, amidate, alkoxide, amide, $BR_4$, $AlR_4$, or alkyl aluminoxane;
R is independently selected at each occurrence thereof from the group consisting of H, $C_6F_5$, phenyl, and $C_{1-6}$ alkyl; and
wherein if Alk is Me, then M is not Y, La, Ce, or Pr; and
polymerizing the unsaturated hydrocarbon monomers in the presence of the catalyst under conditions effective to produce a polymer.

The processes of this invention are used to polymerize any unsaturated hydrocarbon monomer or monomers. Preferred monomers that can be used according to the present invention include olefins, polyenes, and vinyl aromatic hydrocarbons.

Polyenes, particularly dienes and trienes (e.g., myrcene) can be employed in accordance with the present invention. Illustrative polyenes include $C_4$-$C_{30}$ dienes, preferably $C_4$-$C_{12}$ dienes. Preferred among these are conjugated dienes such as, but not limited to, 1,3-butadiene, 1,3-pentadiene, 1,3-hexadiene, 1,3-octadiene, 2,3-dimethyl-1,3-butadiene, 2-ethyl-1,3-butadiene, 2-methyl-1,3-butadiene, 2-methyl-1,3-pentadiene, 3-methyl-1,3-pentadiene, 4-methyl-1,3-pentadiene, 2,4-hexadiene, and the like.

Examples of olefins that can be employed according to the present invention include $C_2$-$C_{30}$ straight chain or branched α-olefins such as ethylene, propylene, 1-butene, 1-pentene, 3-methyl-1-butene, 1-hexene, 4-methyl-1-pentene, 3-methyl-1-pentene, 1-octene, and the like, as well as $C_3$-$C_{30}$ cyclo-olefins such as cyclopentene, cycloheptene, norbornene, 5-methyl-2-norbornene, and tetra-cyclododecene.

Vinyl aromatic hydrocarbons which may be used according to the present invention include vinyl aryl compounds such as, styrene, various alkyl-substituted styrenes, alkoxy-substituted styrenes, 2-vinylpyridine, 4-vinylpyridine, vinyl-naphthalene, alkyl-substituted vinyl napthalenes and the like.

One embodiment relates to the process of the present invention where the unsaturated hydrocarbon monomer is a diene, styrene or ethylene. In one embodiment, the diene is 1,3-butadiene or isoprene. Another embodiment relates to the process of the present invention where the polymer is polybutadiene or polyisoprene.

The catalyst generated under the above conditions is used for the polymerization of unsaturated hydrocarbon monomers to obtain polymers with high 1,4-cis content and high conversion. The non-polar solvent used for the polymerization of unsaturated hydrocarbon monomers should contain at least one or more aliphatic hydrocarbons (e.g., butane, pentane, hexane, isopentane, heptane, octane, and isooctane); cycloaliphatic hydrocarbons (e.g., cyclopentane, methylcyclopentane, cyclohexane, methylcyclohexane, and ethylcyclohexane); aromatic hydrocarbons (e.g., benzene, toluene, ethylbenzene, or xylene).

Another embodiment relates to the process of the present invention where polymerization is carried in a presence of a solvent. In one embodiment, the solvent is a non-polar solvent not reactive with the components of the catalyst system. Examples of suitable solvents include: aliphatic hydrocarbons such as pentane, hexane, isopentane, heptane, octane and isooctane; cycloaliphatic hydrocarbons such as cyclopentane, methyl cyclopentane, cyclohexane, methyl cyclohexane and ethyl cyclohexane; and aromatic hydrocarbons such as benzene, toluene, ethylbenzene and xylene. Preferred non-polar solvents include cyclohexane, hexane, heptane, or toluene.

The polymerization solvent, which can significantly affect polymerization, is used after removal of oxygen and water. Polymerization is initiated in an inert atmosphere (preferably, under high-purity nitrogen atmosphere) and the polymerization temperature is preferably carried out at room temperature to 100° C., more preferably 40° C. to 80° C., most preferably 60° C. Under the appropriate catalyst conditions, the polymerization can be carried out for 10 min to 10 hours, preferably 30 min to 6 hours, most preferably two-hours.

The molar ratio of the unsaturated hydrocarbon monomer to the solvent is 1:1 to 30:1, preferably 2:1 to 10:1. If the molar ratio exceeds the above range, the viscosity of the polymer solution is increased.

Unsaturated hydrocarbon monomers can be added to the reaction mixture in one portion or gradually. When the unsaturated hydrocarbon monomer is gradually added to the reaction mixture, it may be allowed to react for 10 min to 3 hours prior to addition of the next portion of the unsaturated hydrocarbon monomer. More preferably this period can be 15 min to 2 hours, most preferably 15 to 30 min.

The conversion of the unsaturated hydrocarbon monomers to the polymer under the conditions described above is more than 50%, preferably more than 80%, most preferably, more than 90%.

After polymerization is completed, known processes such as catalyst inactivation treatment, catalyst removing treatment, and drying can be performed if required. The polymerization can be completed by introducing a reaction terminator and/or a stabilizer. The resulting polybutadiene can be precipitated, for example, with methanol or ethanol.

The reaction terminators that can be used according to the present invention include polyoxyethyleneglycolether organophosphate, methanol, ethanol, isopropanol, water, or carbon dioxide, organic acids such as octanoic acid, decanoic acid and stearic acid, and the like.

The phenol stabilizers that can be used according to the present invention can be any of known phenol stabilizers having a phenol structure. Examples are 2,6-di-t-butyl-p-cresol, 2,6-di-t-butyl-4-ethylphenol, 2,6-dicyclohexyl-p-cresol, 2,6-diisopropyl-4-ethylphenol, 2,6-di-t-amyl-p-cresol, 2,6-di-t-octyl-4-n-propylphenol, 2,6-dicyclohexyl-4-n-octylphenol, 2-isopropyl-4-methyl-6-t-butylphenol, 2-t-butyl-4-ethyl-6-t-octylphenol, 2-isobutyl-4-ethyl-6-t-hexylphenol, 2-cyclohexyl-4-n-butyl-6-isopropylphenol, 2-t-butyl-6-(3'-t-butyl)-5'-methyl-2'hydroxybenzyl)-4-methylphenylacrylate, t-butylhydroquinone, 2,2'-methylenebis (4-methyl-6-t-butylphenol), 4,4'-butylidenebis(3-methyl-6-t-butylphenol), 4,4'-thiobis(3-methyl-6-t-butylphenol), 2,2'-thiobis(4-methyl-6-t-butylphenol), 4,4'-methylenebis(2,6-di-t-butylphenol), 2,2'-methylenebis[6-(1-methylcyclohexyl)-p-cresol], 2,2'-ethylidenebis(4,6-di-t-butylphenol), 2,2'-butylidenebis(2-t-butyl-p-cresol), 1,1,3-tris(2-methyl-4-hydroxy-5-t-butylphenyl)butane, triethyleneglycol-bis[3-(3-t-butyl-5-methyl-4-hydroxyphenyl)propionate], 1,6-hexanediol-bis[3-(3,5-di-t-butyl-4-hydroxyphenyl)propionate], 2,2-thiodiethylenebis[3-(3,5-di-t-butyl-4-hydroxyphenyl)propionate], n-octadecyl-3-(3',5'-di-t-butyl-4'-hydroxyphenyl)propionate, N,N'-hexamethylenebis(3,5-di-t-butyl-4-hydroxy-hydrocinnamide), 3,5-di-t-butyl-4-hydroxybenzylphosphonate-diethylester, 1,3,5-tris(2,6-dimetyl-3-hydroxy-4-t-butylbenzyl)isocyanurate, 1,3,5-tris[(3,5-di-t-butyl-4-hydroxyphenyl)propyonyloxyethyl] isocyanurate, 2,4-bis(n-octylthio)-6-(4-hydroxy-3,5-di-t-butylanilino)-1,3,5-triazine, tetrakis[methylene-3-(3,5-di-t-butyl-4-hydroxyphenyl)propionate]methane, bis(3,5-di-t-butyl-4-hydroxybenzylphosphonate ethyl)calcium, bis(3,5-di-t-butyl-4-hydroxybenzylphosphoric acid ethyl)nickel, N,N'-bis[3,5-di-t-butyl-4-hydroxyphenyl)propyonyl]hydrazine, 2,2'-methylenebis(4-methyl-6-t-butylphenol)terephthalate, 1,3,5-trimethyl-2,4,6-tris(3,5-di-t-butyl-4-hydroxybenzyl)benzene, 3,9-bis[1,1-dimethyl-2-{3-(3-t-butyl-4-hydroxy-5-methylphenyl)propionyloxy}ethyl]-2,4,8,10-tetraoxaspiro[5,5]undecane, 2,2-bis[4-{2-(3,5-di-t-butyl-4-hydroxyhydrocinnamoyloxy)}ethoxyphenyl]propane, and the like. Preferred stabilizer is 2,6-di-t-butyl-p-cresol.

Another aspect of the present invention relates to a process for polymerizing unsaturated hydrocarbon monomers. This process includes providing unsaturated hydrocarbon monomers; providing a catalyst, wherein the catalyst is prepared by the process comprising:

providing a precatalyst having the structure of Formula (I):

$$M\{C(SiHAlk_2)_3\}_3 \quad (I),$$

wherein

M is a lanthanide or a transition metal; and

Alk is $C_{1-6}$ alkyl;

reacting the precatalyst of Formula (I) under conditions effective to produce the catalyst; and polymerizing the unsaturated hydrocarbon monomers in the presence of the catalyst under conditions effective to produce polymer. Optionally, if Alk is Me, then M is not Y, La, Ce, or Pr.

One embodiment relates to the process of the present invention, where said reacting comprises reacting the precatalyst with a Lewis acid and/or an alkylaluminum reagent under conditions effective to produce the catalyst. Another embodiment relates to the process of the present invention, where said reacting comprises reacting the precatalyst with an alkylaluminum reagent and/or a halide source under conditions effective to produce the catalyst. Yet another embodiment relates to the process of the present invention, where said reacting comprises reacting the precatalyst with a Lewis acid and/or a halide source under conditions effective to produce the catalyst.

The molar ratio of the precatalyst to the alkylaluminum reagent is 1:1 to 1:300, preferably 1:10 to 1:200.

The molar ratio of the precatalyst to the halide source is 1:1 to 1:200, preferably 1:10 to 1:150.

The molar ratio of the precatalyst to the Lewis acid is 1:1 to 1:200, preferably 1:10 to 1:150.

One embodiment relates to the process of the present invention where the alkylaluminum reagent is selected from the group consisting of triisobutylaluminium (TIBA), methylaluminoxane (MAO), modified methylaluminoxane (MMAO), ethylaluminoxane, propylaluminoxane, isopropylaluminoxane, butyl aluminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentyl aluminoxane, phenylaluminoxane, 2,6-dimethylphenylaluminoxane, trimethylaluminum, tripropylaluminum, trihexylaluminum, trioctylaluminum, triethylaluminum, triisoprenylaluminum, tris(2-ethylhexyl)aluminum, tricyclohexylaluminum, tris(1- methylcyclopentylaluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, ethyldibenzylaluminum, triisopropylaluminum, tributylaluminum, tripentylaluminum, diazobythylaluminum hydride, diethylaluminum hydride, diisopropylaluminum hydride, dibutylaluminum hydride, diisobutylaluminum hydride, dioctylaluminumhydride, diphenylaluminum hydride, di-p-tolylaluminum hydride, dibenzylaluminum hydride, phenylethylaluminum hydride, phenylpropylaluminum hydride, phenylisopropylaluminum hydride, phenylbutylaluminum hydride, phenylisobutylaluminum hydride, phenyloctylaluminum hydride, p-tolyl ethylaluminum hydride, p-tolylpropylaluminum hydride, p-tolylisopropylaluminum hydride, p-tolylbutylaluminum hydride, p-tolylisobutylaluminum hydride, p-tolyloctylaluminum hydride, benzylethylaluminum hydride, benzylpropylaluminum hydride, benzylisopropylaluminum hydride, benzylbutylaluminum hydride, benzylisobutylaluminum hydride, and benzyloctylaluminum hydride.

Another embodiment relates to the process of the present invention where the Lewis acid is selected from the group consisting of [Ph$_3$C][B(C$_6$F$_5$)$_4$], B(C$_6$F$_5$)$_3$, Ph$_3$B, PhB(C$_6$H$_5$)$_2$, Ph$_3$CCl, methylaluminoxane (MAO), modified methylaluminoxane (MMAO), ethylaluminoxane, propylaluminoxane, isopropylaluminoxane, butylauminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentyl aluminoxane, phenylaluminoxane, 2,6-dimethylphenylaluminoxane, ethylaluminum sesquichloride, diisobutylaluminum chloride, di ethylaluminum chloride, ethylaluminum dichloride, ethylaluminum sesquichloride, isobutylaluminum dichloride, dimethylaluminum chloride, isobutylaluminum dichloride, diethylaluminum iodide, diethylaluminum chloride, diisopropylaluminum chloride, diisobutylaluminum chloride, dioctylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenylbutylaluminum chloride, phenylisobutylaluminum chloride, phenyloctylaluminum chloride, p-tolylethylaluminum chloride, p-tolylpropylaluminum chloride, p-tolylisopropylaluminum chloride, p-tolylbutylaluminum chloride, p-tolylisobutylaluminum chloride, p-tolyloctylaluminum chloride, benzyl ethylaluminum chloride, benzylpropylaluminum chloride, benzylisopropylaluminum chloride, benzylbutylaluminum chloride, benzylisobutylaluminum chloride, benzyloctylaluminum chloride, propylaluminum dichloride, isopropylaluminum dichloride, butylaluminum dichloride, isobutylaluminum dichloride, and octylaluminum dichloride. In one embodiment Lewis acid is an alkylaluminum halide.

Yet another embodiment relates to the process of the present invention where the halide source is Ph$_3$C-Hal, N-chlorosuccinimide, [Alk$_3$NH][Hal], or an electrophilic chlorine source, wherein Hal is halogen and each Alkyl is independently selected in each occurrence thereof from C$_{1-6}$ alkyl.

Examples

Example 1—Materials and Methods

All manipulations were performed under a dry argon atmosphere using standard Schlenk techniques or under a nitrogen atmosphere in a glovebox unless otherwise indicated. Water and oxygen were removed from benzene and pentane solvents using an IT PureSolv system. Benzene-d$_6$ was heated to reflux over Na/K alloy and vacuum-transferred. The compound NdI$_3$(THF)$_3$ was prepared based upon literature procedures (Deacon et al., *Australian J. of Chem.* 53:853-865 (2000); Hazin et al., *Organometallics* 6:23-27 (1987), which are hereby incorporated by reference in their entirety), KC(SiHMe$_2$)$_3$ (Evans et al., *J. Am. Chem. Soc.* 104:2015-2017 (1982), which is hereby incorporated by reference in its entirety), B(C$_6$F$_5$)$_3$ (Massey et al., *J. Organomet. Chem.* 2:245-250 (1964), which is hereby incorporated by reference in its entirety) were prepared following literature procedures.

$^1$H, $^{13}$C{$^1$H}, $^{11}$B, and $^{29}$Si{$^1$H} NMR spectra were collected on a Bruker DRX-400 spectrometer, a Bruker Avance 111-600 spectrometer, or an Agilent MR 400 spectrometer. $^{11}$B NMR spectra were referenced to an external sample of BF$_3$.Et$_2$O. Infrared spectra were measured on a Bruker Vertex 80. Elemental analyses were performed using a Perkin-Elmer 2400 Series II CHN/S. X-ray diffraction data was collected on a Bruker APEX II diffractometer.

Example 2—Synthesis of Nd{C(SiHMe$_2$)$_3$}$_3$ (1d)

NdI$_3$(THF)$_3$ (0.204 g, 0.275 mmol) and KC(SiHMe$_2$)$_3$ (0.189 g, 0.827 mmol) were stirred in benzene (10 mL) at room temperature for 12 hours. Evaporation of the volatile materials, pentane extraction (3×5 mL), and evaporation of the pentane afforded a spectroscopically pure sticky yellow solid (0.176 g, 0.247 mmol, 89.7%). This solid was recrystallized at −30° C. from a minimal amount of pentane to obtain 1d as colorless crystals. This solid was recrystallized at −30° C. from a minimal amount of pentane to obtain 1d as blue-green crystals. $^1$H NMR (benzene-d$_6$, 600 MHz, 25° C.): δ 27.8 (br, SiH), 1.78 (br, SiMe$_2$). IR (KBr, cm$^{-1}$): 2954 s, 2900 s, 2108 s ($v_{SiH}$), 1829 s br ($v_{SiH}$), 1418 w, 1253 s, 1192 s br, 1058 br, 952 s br, 886 s, 835 w, 778 s, 689 s. Anal. Calcd. for C$_2$, H$_{63}$Si$_9$Nd: C, 35.39; H, 8.91. Found: C, 35.48; H, 9.11. Mp, 119-122° C.

Example 3—Synthesis of Nd{C(SiDMe$_2$)$_3$}$_3$

NdI$_3$(THF)$_3$ (0.183 g, 0.248 mmol) and KC(SiDMe$_2$)$_3$ (0.172 g, 0.743 mmol) were stirred in benzene (10 mL) at room temperature for 12 hours. Evaporation of the volatile materials, pentane extraction (3×5 mL), and evaporation of the pentane afforded a spectroscopically pure sticky yellow solid (0.165 g, 0.229 mmol, 92.2%). This solid was recrystallized at −30° C. from a minimal amount of pentane to obtain 1d-d$_9$ as colorless crystals. $^1$H NMR (benzene, 600 MHz, 25° C.): δ 1.7 (br, SiMe$_2$). $^1$H NMR (toluene-d$_8$, 600 MHz, −79° C.): δ 15.4 (s, SiMe$_2$), 14.6 (s, SiMe$_2$), −17.5 (s, SiMe$_2$). IR (KBr, cm$^{-1}$): 2953 s, 2898 s, 2798 s, 1528 s ($v_{SiD}$), 1467 s, 1408 s, 1328 s ($v_{SiD}$), 1251 s, 1155 s, 939 br, 898 br, 833 s, 812 s, 779 s.

Example 4—Synthesis of Nd{N(SiHMe$_2$)$_2$}$_3$

Nd{C(SiHMe$_2$)$_3$}$_3$ (0.121 g, 0.168 mmol) and HN(SiHMe$_2$)$_2$ (0.067 g, 0.504 mmol) were stirred in pentane (3 mL) at room temperature for 1 hour. The volatile materials were evaporated, the residue was extracted with hexamethyldisiloxane (2×2 mL), and evaporation of the hexamethyldisiloxane afforded analytically pure Nd{N(SiHMe$_2$)$_2$}$_3$ as a sticky yellow-green solid (0.069 g, 0.127 mmol, 75.6%) $^1$H NMR (toluene-d$_8$, 600 MHz, 25° C.): δ 6.12 (br, SiMe$_2$), 5.29 (br, SiH), 0.97 (br, SiH). IR (KBr, cm$^{-1}$): 2954 s, 2899 m, 2855 w, 2091 s br ($v_{SiH}$), 1922 s br ($v_{SiH}$), 1416 w, 1250 s, 1177 m, 1046 s br, 895 s, 837 s, 798 s, 764 s, 688 s, 628 m, 596 m. Anal. Calcd. for $C_{12}H_{42}Si_6N_3Nd$: C, 26.63; H, 7.82; N, 7.76. Found: C, 26.71; H, 7.57; N, 7.67. Mp, 123-125° C.

Example 5—Synthesis of Nd{C(SiHMe$_2$)$_3$}$_2$HB(C$_6$F$_5$)$_3$

B(C$_6$F$_5$)$_3$ (0.033 g, 0.065 mmol) was added to a benzene (4 mL) solution of Nd{C(SiHMe$_2$)$_3$}$_3$ (0.046 g, 0.065 mmol) in small portions. The resulting yellow mixture was stirred at room temperature for 30 min. The solvent was evaporated under reduced pressure to give a yellow paste. The residue was washed with pentane (3×5 mL) and the volatiles were evaporated to dryness in vacuo to give Nd{C(SiHMe$_2$)$_3$}$_2$HB(C$_6$F$_5$)$_3$ as a green solid (0.057 g, 0.055 mmol, 84.7%). $^1$H NMR (benzene-d$_6$, 600 MHz, 25° C.): δ 5.63 (SiMe$_2$). $^{11}$B NMR (benzene-d$_6$, 119.3 MHz, 25° C.): 6-4.2 (s). $^{19}$F NMR (benzene-d$_6$, 564 MHz, 25° C.): δ−156.6 (3 F, para-C$_6$F$_5$)), −162.9 (6 F, meta-C$_6$F$_5$). IR (KBr, cm$^{-1}$): 2959 m, 2904 w, 2255 m br ($v_{BH}$), 2114 s ($v_{SiH}$), 1792 m br ($v_{SiH}$), 1646 m, 1605 w, 1516 s, 1467 s br, 1372 m, 1258 s, 1110 s br, 1080 s br, 972 s br, 960 s br, 894 s br, 835 br, 786 s, 681 m. Anal. Calcd. for BC$_{32}$F$_{15}$H$_{43}$Si$_6$Nd: C, 37.24; H, 4.20. Found: C, 37.51; H, 4.56. mp=178° C. dec.

Example 6—Synthesis of Nd{C(SiDMe$_2$)$_3$}$_2$DB(C$_6$F$_5$)$_3$

B(C$_6$F$_5$)$_3$ (0.102 g, 0.200 mmol) was added to a benzene (4 mL) solution of Nd{C(SiDMe$_2$)$_3$}$_3$ (0.144 g, 0.200 mmol) in small portions. The resulting yellow mixture was stirred at room temperature for 30 min. The solvent was evaporated under reduced pressure to give a yellow paste. The residue was washed with pentane (3×5 mL) and the volatiles were evaporated to dryness in vacuo to give Nd{C(SiDMe$_2$)$_3$}$_2$DB(C$_6$F$_5$)$_3$ as a green solid (0.152 g, 0.146 mmol, 48.9%). $^1$H NMR (benzene, 600 MHz, 25° C.): δ 5.59 (br, SiMe$_2$). $^{11}$B NMR (benzene, 119.3 MHz, 25° C.): δ−4.0 (br). $^{19}$F NMR (benzene, 564 MHz, 25° C.): δ−156.6 (3 F, para-C$_6$F$_5$), −162.9 (6 F, meta-C$_6$F$_5$). IR (KBr, cm$^{-1}$): 2959 m, 2903 w, 1646 br, 1607 br, 1516 s br, 1467 s br, 1370 br, 1312 br, 1258 br, 1101 s br, 1080 s br, 977 s br, 892 s br, 841 s.

Example 7—Synthesis of Nd(C(SiHMe$_2$)$_3$)$_2$HB(C$_6$F$_5$)$_3$(pyr)

Nd(C(SiHMe$_2$)$_3$)$_2$HB(C$_6$F$_5$)$_3$ (0.530 g, 0.514 mmol) and pyridine (0.041 g, 0.514 mmol) were stirred in 5 mL of benzene at 25° C. for 1 hour. Evaporation of benzene solvent followed by pentane wash (2×5 mL), and evaporation of the pentane afforded a pale yellow solid of Nd(C(SiHMe$_2$)$_3$)$_2$HB(C$_6$F$_5$)$_3$(pyr) which was spectroscopically pure (0.584 g, 0.433 mmol, 84.4%). $^1$H NMR (benzene-d$_6$, 600 MHz, 25° C.): δ 12.17 (br, SiH), 11.01 (s, 2H, NC$_5$H$_5$), 10.29 (s, 1H, NC$_5$H$_5$), 5.08 (s, 2H, NC$_5$H$_5$), 4.27 (s, SiMe$_2$). $^{11}$B NMR (benzene-d$_6$, 119.3 MHz, 25° C.): δ−25.9 (br). $^{19}$F NMR (benzene-d$_6$, 564 MHz, 25° C.): δ 133.9 (6 F, ortho-C$_6$F$_5$), −164.26 (3 F, para-C$_6$F$_5$), −167.34 (6 F, meta-C$_6$F$_5$). IR (KBr, cm$^{-1}$): 2960 s, 2902 s, 2272 s ($v_{BH}$), 2113 s ($v_{SiH}$), 1863 s br ($v_{SiH}$), 1699 s, 1643 s, 1602 s, 1512 s, 1465 s, 1373 s, 1275 s, 1257 s, 1222 m, 1105 s br, 1069 w, 1039 s, 1005 s, 970 s br, 896 br, 840 br, 786 s, 753 s, 701 s, 680 s, 624 s, 603 s, 567 s, 507 s, 467 s. Anal. Calcd for C$_{37}$H$_{48}$BF$_{15}$NdNSi$_6$: C, 40.04; H, 4.36; N, 1.26. Found: C, 39.98; H, 4.31; N, 1.20. mp=170-172° C.

Example 8—Synthesis of Nd{C(SiHMe$_2$)$_3$}{HB(C$_6$F$_5$)$_3$}$_2$

B(C$_6$F$_5$)$_3$ (0.067 g, 0.132 mmol) was added to a benzene (4 mL) solution of Nd{C(SiHMe$_2$)$_3$}$_3$ (0.047 g, 0.066 mmol) in small portions. The resulting yellow mixture was stirred at room temperature for 30 min. The solvent was evaporated under reduced pressure to give a yellow paste. The residue was washed with pentane (3×5 mL) and the volatiles were evaporated to dryness in vacuo to give Nd{C(SiHMe$_2$)$_3$}{HB(C$_6$F$_5$)$_3$}$_2$ as a green solid (0.076 g, 0.056 mmol, 84.8%). $^1$H NMR (benzene-d$_6$, 600 MHz, 25° C.): δ 10.69 (C$_7$H$_8$), 8.29 (SiMe$_2$), 5.43 (C$_7$H$_8$), 2.92 (C$_7$H$_8$), −3.63 (C$_7$H$_8$). $^{13}$C{$^1$H} NMR (benzene-d$_6$, 150 MHz, 25° C.): δ 132.03 (C$_6$F$_5$), −1.12 (SiMe$_2$). $^{11}$B NMR (benzene-d$_6$, 119.3 MHz, 25° C.): δ 25.1 (s). $^{19}$F NMR (benzene-d$_6$, 564 MHz, 25° C.): δ−154.24 (3 F, para-C$_6$F$_5$), −161.76 (6 F, meta-C$_6$F$_5$). IR (KBr, cm$^{-1}$): 2963 m, 2257 m br ($v_{BH}$), 2111 s ($v_{SiH}$), 1648 m, 1606 w, 1518 s, 1467 s br, 1372 m, 1282 s, 1266 s br, 1116 s br, 1081 s br, 973 s br, 954 s br, 895 s br, 842 br, 790 s. Anal. Calcd. for B$_2$C$_{43}$F$_{30}$H$_{23}$Si$_3$Nd: C, 37.98; H, 1.71. Found: C, 38.09; H, 1.92. mp=181-184° C.

Example 9—Synthesis of Nd{C(SiDMe$_2$)$_3$}{DB(C$_6$F$_5$)$_3$}$_2$

B(C$_6$F$_5$)$_3$ (0.087 g, 0.170 mmol) was added to a benzene (4 mL) solution of Nd{C(SiDMe$_2$)$_3$}$_3$ (0.061 g, 0.085 mmol) in small portions. The resulting yellow mixture was stirred at room temperature for 30 min. The solvent was evaporated under reduced pressure to give a yellow paste. The residue was washed with pentane (3×5 mL) and the volatiles were evaporated to dryness in vacuo to give NdC(SiDMe$_2$)$_3${DB(C$_6$F$_5$)$_3$}$_2$ as a green solid (0.098 g, 0.072 mmol, 85.0%). $^1$H NMR (benzene-d$_6$, 600 MHz, 25° C.): δ 8.29 (br, SiMe$_2$). $^{11}$B NMR (benzene, 119.3 MHz, 25° C.): δ 37.8 (s). $^{19}$F NMR (benzene, 564 MHz, 25° C.): δ−153.4 (3 F, para-C$_6$F$_5$), −162.3 (6 F, meta-C$_6$F$_5$). IR (KBr, cm$^{-1}$): 2962 m, 2907 w, 1648 s, 1607 w, 1517 s br, 1465 s br, 1371 m, 1282 s br, 1261 s br, 1124 s br, 1102 s br, 1082 s br, 975 s br, 943 s br, 880 s br, 845 s br, 799 s br, 704 m.

Example 10—Discussion of Examples 1-9

Synthesis and Characterization of Nd{C(SiHMe$_2$)$_3$}$_3$.

The homoleptic neodymium tris(alkyl) complexes were synthesized by reaction of NdI$_3$(THF)$_3$ and 3 equiv. of KC(SiHMe$_2$)$_3$ in benzene for 12 hours at room temperature. Nd{C(SiHMe$_2$)$_3$}$_3$ formed blue block-like crystals from pentane. In contrast to neodymium iodide precursors, the combination of anhydrous rare earth chloride NdCl$_3$ and KC(SiHMe$_2$)$_3$ in benzene or THF at room temperature does not provide the corresponding organometallic compounds.

(1)

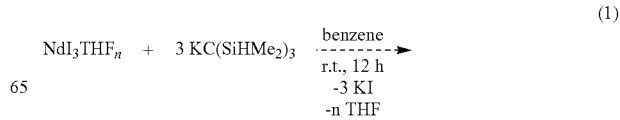

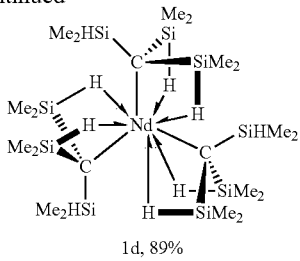

1d, 89%

The selectively isotopically labeled Nd{C(SiDMe$_2$)$_3$}$_3$ (eq. 2) was also synthesized from KC(SiDMe$_2$)$_3$ (Yan et al., *Organometallics* 32:1300-1316 (2013), which is hereby incorporated by reference in its entirety) to facilitate the characterization of Nd{C(SiDMe$_2$)$_3$}$_3$ and study its fluxional processes.

(2)

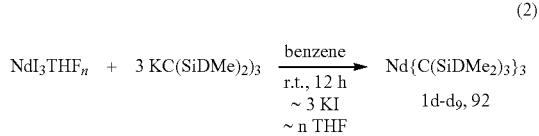

The room temperature $^1$H NMR spectra of Nd{C(SiHMe$_2$)$_3$}$_3$ contained two $^1$H NMR resonances, but no signals were detected in $^{13}$C or $^{29}$Si NMR spectra using direct or indirect detection methods. Broad $^1$H NMR signals with similar chemical shifts of 1.78 ppm (775 Hz at half-height) were measured and assigned to silylmethyl groups on the basis of their integration of 6H with respect to the second peak. The second peak, which was attributed to the SiH group, exhibited a large averaged paramagnetic chemical shift for Nd (27.8 ppm). The assignments were supported by the spectra of the deuterium-labelled compounds, which showed a SiMe$_2$ peak at 1.7 ppm for Nd{C(SiDMe$_2$)$_3$}$_3$. Only four resonances were resolved in the low temperature $^1$H NMR spectra of Nd{C(SiHMe$_2$)$_3$}$_3$.

The $v_{SiH}$ region from 1800-2200 cm$^{-1}$ of the IR was particularly informative. A band at ca. 2107 cm$^{-1}$ was assigned to the stretching mode of a 2-center-2-electron SiH group. The compound also contained a second, lower energy band at ~1830 cm$^{-1}$ assigned to the SiH mode in a three-center-two-electron Ln ⎯ H—Si moiety. The assignment of both of these bands as $v_{SiH}$ was supported by isotopically labeled samples Nd{C(SiDMe$_2$)$_3$}$_3$, which contained two bands $v_{SiD}$ at ~1529-30 and 1324-29 cm$^{-1}$ while the $v_{SiH}$ bands noted above were not observed.

Nd{C(SiHMe$_2$)$_3$}$_3$ was highly crystalline, and a single crystal X-ray diffraction experiments provided the molecular structure shown in FIG. 1.

In addition, these homoleptic tris(alkyl) lanthanides could be starting materials for other rare earth compounds. Their reactions with amines were explored. Nd{C(SiHMe$_2$)$_3$}$_3$ and 3 equiv. of tetramethyldisilazide were reacted at room temperature to yield Ln{N(SiHMe$_2$)$_2$}$_3$ quantitatively.

(3)

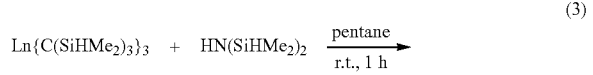

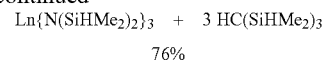

76%

The IR spectrum of Nd{N(SiHMe$_2$)$_2$}$_3$ showed two $v_{SiH}$ at 2091 and 1922 cm$^{-1}$ for classical and non-classical SiH interactions.

Reaction with One Equiv. Of B(C$_6$F$_5$)$_3$

Nd{C(SiHMe$_2$)$_3$}$_3$ did not react with butadiene under normal conditions (excess butadiene, 60° C.) to give polybutadiene. The activation was studied based on the hypothesis that catalytically active Nd butadiene polymerization occurs with [RNd]$^{2+}$ species. Moreover, the goal to obtain a single-site precatalyst for butadiene polymerization requires detailed investigation of the reaction of activators, primarily Lewis acids, but also halide sources and aluminum reagents.

Lewis acids, such as B(C$_6$F$_5$)$_3$ are known to abstract an alkyl group generating cationic alkyl complexes of rare earth metals (Zeimentz et al., *Chem. Rev.* 106:2404-2433 (2006), which is hereby incorporated by reference in its entirety) which are of interest due to their enhanced electrophilicity and application in homogeneous catalysis and polymerization reactions (Kramer et al., *Eur. J. Inorg. Chem.* 665-674 (2007); Arndt et al., *Angew. Chem. Int. Ed.* 42:5075-5079 (2003), which are hereby incorporated by reference in their entirety). The abstraction reaction by Lewis acid creates a free coordination site on the metal center which makes it active for various catalytic and olefin polymerization reactions.

The reactions of Nd{C(SiHMe$_2$)$_3$}$_3$ and one equiv. of B(C$_6$F$_5$)$_3$ yielded Nd{C(SiHMe$_2$)$_3$}$_2$HB(C$_6$F$_5$)$_3$ and 0.5 equiv. of the disilacyclobutane [(Me$_2$HSi)$_2$C—SiMe$_2$]$_2$, which is formally the head-to-tail dimer of the silene (Me$_2$HSi)$_2$C=SiMe$_2$.

(4)

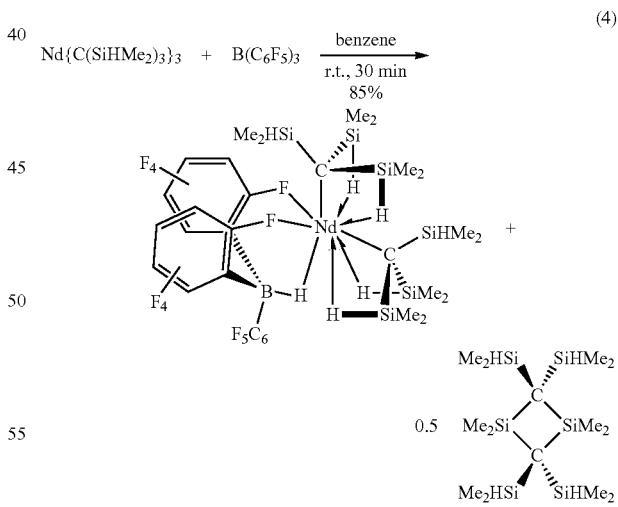

The $^{11}$B NMR spectrum contained paramagnetically shifted broad signals at −4 ppm, respectively, indicating that the {(Me$_2$HSi)$_3$C}$_2$Nd$^+$ and HB(C$_6$F$_5$)$_3$ groups interact in solution. In addition, $^1$H NMR spectrum contained only one signal at 5.6 ppm corresponding to SiMe$_2$. The $^1$H NMR spectra of the corresponding {(Me$_2$DSi)$_3$C}$_2$NdDB(C$_6$F$_5$)$_3$ showed a SiMe$_2$ peak 5.6 ppm (Nd) which supported the assignment.

In the $^{19}$F NMR spectrum of {(Me$_2$HSi)$_3$C}$_2$NdHB(C$_6$F$_5$)$_3$ measured at room temperature, only two signals were detected (e.g., −157.1 and −162.4 ppm) in a 1:2 ratio assigned to para and meta fluorine on the C$_6$F$_5$.

On adding donor ligands, such as pyridine to Nd(C(SiHMe$_2$)$_3$)$_2$HB(C$_6$F$_5$)$_3$, $^{11}$B NMR shifted from −18 to −23.6 ppm for La(C(SiHMe$_2$)$_3$)$_2$HB(C$_6$F$_5$)$_3$ while for the paramagnetic compounds it shifted from −4 to −25.9 ppm for Nd(C(SiHMe$_2$)$_3$)$_2$HB(C$_6$F$_5$)$_3$ suggesting that the HB(C$_6$F$_5$)$_3$ group is far from the paramagnetic influence of the metal center. This fact is also supported by $^{19}$F NMR where three $^{19}$F signals are observed at −133.9 ppm (ortho), −164.3 ppm (para) and −167.3 ppm (meta).

As in the neutral compounds, IR spectroscopy was useful. Two $\nu_{SiH}$ bands were observed at 2113 and 1792 cm$^{-1}$ for {(Me$_2$HSi)$_3$C}$_2$NdHB(C$_6$F$_5$)$_3$ which suggested the presence of classical and non-classical interactions within the structure. In addition, a band at 2255 cm$^{-1}$ was assigned to the $\nu_{BH}$, providing strong support for H abstraction. These signals were not observed in Nd{C(SiDMe$_2$)$_3$}$_2$DB(C$_6$F$_5$)$_3$, and corresponding $\nu_{BD}$ and $\nu_{SiD}$ overlapped with signals from the B(C$_6$F$_5$)$_3$ group and were not assigned.

Reaction with Two Equiv. Of B(C$_6$F$_5$)$_3$

The reactions of Nd{C(SiHMe$_2$)$_3$}$_3$ and two equiv. of B(C$_6$F$_5$)$_3$ resulted in dicationic NdC(SiHMe$_2$)$_3$(HB(C$_6$F$_5$)$_3$)$_2$ and 1 equiv. of disilacyclobutane [(Me$_2$SiH)$_2$C—SiMe$_2$]$_2$ via β hydrogen abstraction.

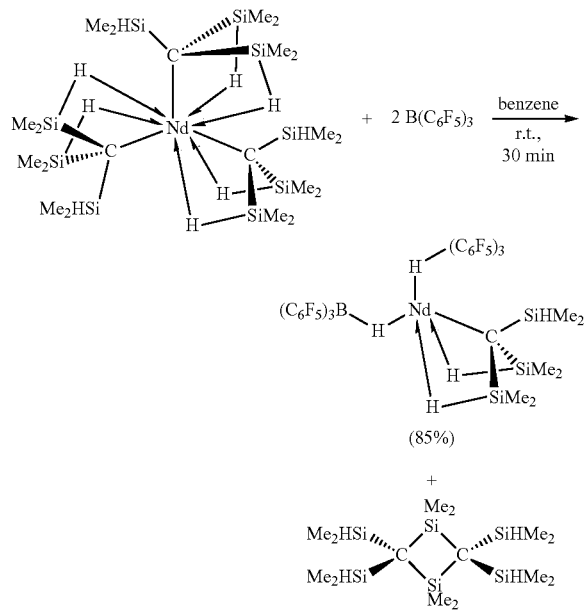

NdC(SiHMe$_2$)$_3$(HB(C$_6$F$_5$)$_3$)$_2$ was catalytically active for the polymerization of butadiene (see below). In addition, the dicationic product was characterized as a toluene adduct through a single crystal X-ray diffraction study, as well as spectroscopically ($^1$H and $^{11}$B NMR and IR). Moreover, the product NdC(SiHMe$_2$)$_3$[HB(C$_6$F$_5$)$_3$]$_2$ was soluble in aliphatic hydrocarbon solvents such as pentane, cyclohexane, and decane. It could be added directly to the catalytic reaction mixture.

The $^1$H NMR spectrum for the paramagnetic compounds NdC(SiHMe$_2$)$_3$(HB(C$_6$F$_5$)$_3$)$_2$, SiMe$_2$ appeared as a broad signal at 8.29 ppm while no SiH peak was observed. The SiMe$_2$ chemical shifts were confirmed by $^1$H NMR of deuterium labelled. The $^{11}$B NMR resonance was observed at 25.1 ppm.

A single crystal X-ray diffraction study revealed that one C(SiHMe$_2$)$_3$ ligand is coordinated to the Nd center while the other two coordination sites are taken up by tridentate HB(C$_6$F$_5$)$_3$ group. The C(SiHMe$_2$)$_3$ ligand is oriented such that two non-classical SiH's face the Nd center. There are a total of three Nd—F interactions in the molecule including two bridging ortho-F atoms of one B(C$_6$F$_5$)$_3$ group and one bridging ortho-F atom from the other B(C$_6$F$_5$)$_3$ group. The Nd—F bond distances are 2.616(6) Å, 2.857(6) Å from one B(C$_6$F$_5$)$_3$ group and 2.600(7) Å from other B(C$_6$F$_5$)$_3$ group. These bond distances are similar to the one observed in the crystal structure of Ce(C(SiHMe$_2$)$_3$)$_2$HB(C$_6$F$_5$)$_3$. In addition to one C(SiHMe$_2$)$_3$ group and two B(C$_6$F$_5$)$_3$ groups, a toluene molecule also coordinates to the Nd center. The coordination of crystallization solvent molecule in the crystal structure of Nd compounds is not unusual as coordinated toluene was observed in (η-C$_6$H$_5$Me)Nd[N(C$_6$F$_5$)$_2$]$_3$ (Click et al., Chem. Commun. 633-634 (1999), which is hereby incorporated by reference in its entirety). Also, the compound co-crystallizes with benzene molecule. The bond distances of Nd—C(toluene) ranged between 2.954(13) to 3.026(12) Å which is shorter than Nd—C(toluene) bond distances in (η-C$_6$H$_5$Me)Nd[N(C$_6$F$_5$)$_2$]$_3$ (Click et al., Chem. Commun. 633-634 (1999), which is hereby incorporated by reference in its entirety) (2.98(2) to 3.324(13) Å) suggesting a stronger coordination of toluene molecule. The Nd—C bond distance is ca. 0.11 Å shorter than those in the present Nd compound suggesting the positive charge generated on the Nd center due to Lewis acid abstraction of two alkyl groups causes the molecule to shrink. Similarly, Nd—Si bond distances also shorten to 3.135(3) and 3.101(4) Å from av. 3.152 Å. There are no other crystallographically characterized Nd alkyl borates reported in literature.

Example 11—Reaction Between Nd{C(SiHMe$_2$)$_3$}$_3$ and [Ph$_3$C][B(C$_6$F$_5$)$_4$]

Alternatively, Nd{C(SiHMe$_2$)$_3$}$_3$ and the strong Lewis acid [Ph$_3$C][B(C$_6$F$_5$)$_4$] reacted to give Ph$_3$CH and 1,3-disilacyclobutane. Unlike the B(C$_6$F$_5$)$_3$ reaction, the presumed [RNd]$^{2+}$ product was not crystallographically characterized and was not readily isolated. Instead, the reaction of [Ph$_3$C][B(C$_6$F$_5$)$_4$] and Nd{C(SiHMe$_2$)$_3$}$_3$ was performed in situ to generate a catalytically active species.

It was found that simple halide sources such as Ph$_3$CCl, n-chlorosuccinimide, and [nBu$_3$NH]Cl provided hydrocarbon soluble and catalytically active neodymium polymerization catalysts (upon addition of alkylaluminum reagents). It was found that diisobutylaluminum chloride does not appear to be a good chloride source in terms of providing catalytically active neodymium species.

Addition of 2 equivalents of Ph$_3$CCl to Nd{C(SiHMe$_2$)$_3$}$_3$ generated only one equivalent of Ph$_3$CH. This result contrasted the [Ph$_3$C][B(C$_6$F$_5$)$_4$] which gave stoichiometric amounts (two equiv.) of Ph$_3$CH. A new organic species was found, which contained Si—H signals in the NMR. That organic species was independently synthesized and assigned to be Ph$_2$C=C$_6$H$_5$C(SiHMe$_2$)$_3$, resulting from nucleophilic attack on the aromatic of the trityl cation by an alkyl ligand. Small amounts of the disilacyclobutane by-product of SiH abstraction can be also identified. The neodymium product was neither isolated nor spectroscopically assigned (by NMR or IR), but notably the reaction mixture was homogeneous even in heptane or cyclohexane.

Assuming NdC(SiHMe$_2$)$_3$Cl$_2$ was formed (based on expected stoichiometry), it was notably soluble. Alternatively, a species with Nd{C(SiClMe$_2$)(SiHMe$_2$)$_2$} groups was also possible to account for Ph$_3$CH present in the reaction mixture.

Example 12—Polymerization Studies

After studying the activation of our complexes, the butadiene polymerization chemistry of Nd{C(SiHMe$_2$)$_3$}$_3$ was tested. The important reactions are shown in Table 1 below.

TABLE 1

| RXN# | Precatalyst Conditions$^a$ | Vinyl:Trans:Cis | Mn | Mw | PDI | General Reactivity |
|---|---|---|---|---|---|---|
| 611 | [Nd] + 2 [Ph$_3$C][B(C$_6$F$_5$)$_4$] + 200 TIBA (Tol) | 5:44:51 | 8.2 | 18.9 | 2.3 | High |
| 605 | [Nd] + 2 [Ph$_3$C][B(C$_6$F$_5$)$_4$] + 10 TIBA (Tol) | 3:34:63 | 7.4 | 15.8 | 2.1 | Low-Mod |
| 614 | [Nd] + 2B (C$_6$F$_5$)$_3$ + 50 TIBA (Tol) | ~0:50:50 (NMR) | | | | High |
| 619 | [Nd] + 2 B(C$_6$F$_5$)$_3$ + 50 TIBA (Heptane) | 2:50:48 | | | | High |
| 622 | [Nd] + 2 Ph$_3$CCl + 50 TIBA (Heptane) | 12:8:80 | | | | Moderate |
| 649 | [Nd] + 2 Ph$_3$CCl + 50 TIBA (Cyclohexane) | ??(Still high Cis) | | | | Moderate |

$^a$Reactions were performed with Nd{C(SiHMe$_2$)}$_3$, Lewis acid, and AlR3 reagent. Butadiene was added to the catalytic mixture 3x at 60° C. Each charge of butadiene was allowed to react for 15-30 minutes.
$^b$Mn, Mw, and PDI are reported for select samples.
$^c$Selectivity (1,2-insertion:1,4-trans insertion:1,4-cis insertion) ratios are based on integrated peaks of IR spectra of the isolated polymer product.
$^d$Reactivity is assessed on amount of polymer isolated.

In the first two experiments, the cis:trans selectivity increased with the decreasing ratio of TIBA to catalyst. However isolated polymer yield and overall catalytic activity decreased dramatically with decreased amounts of triisobutylaluminum.

The mixture of B(C$_6$F$_5$)$_3$ as Lewis acid and triisobutylaluminum gave a highly active catalytic species, but poor cis-trans selectivity. Notably, catalytic activity was high under these conditions both in toluene and in heptane.

It is known from the literature that halide donors (especially chloride) will increase the cis:trans ratio. It was determined that Ph$_3$CCl rather than the more expensive B(C$_6$F$_5$)$_3$ or [Ph$_3$C][B(C$_6$F$_5$)$_4$] was able to activate Nd{C(SiHMe$_2$)$_3$}$_3$ as a precatalyst. With Ph$_3$CCl, the other Lewis acid was not needed, and Ph$_3$CCl was both a halide donor and a catalyst activator (see above). Moreover, there was a significant increase in cis-1,4-insertion obtained with Ph$_3$CCl as the activator.

The catalytic activity and selectivity (in terms of cis:trans properties of the resulting polymers) using other chloride sources, was assessed with B(C$_6$F$_5$)$_3$ or MAO as the Lewis acid. Results are shown in Table 2 below.

TABLE 2

| RXN# | Precatalyst Conditions | Vinyl:Trans:Cis | General Reactivity |
|---|---|---|---|
| | [Nd] + 100 MAO (Cyclohexane) | — | No isolated polymer |
| 699 | [Nd] + 100 MAO (Tol) | 3:68:29 | Moderate |
| 698 | [Nd] + 2 Ph$_3$CCl + 100 MAO (Tol) | 1:11:88 | High |
| 708 | [Nd] + 100 MAO + 2 Ph$_3$CCl (Tol) | 1:14:85 | High |
| 715 | [Nd] + 2 B(C$_6$F$_5$)$_3$ + 2 NCS + 100 MAO (Tol) | 5:20:75 | Moderate |

Nd{C(SiHMe$_2$)$_3$}$_3$, Lewis acid, and chloride source, followed by three charges of BD at 60 C., each charge was allowed to react for 30 minutes. The reagents are given in the order in which they are added to the reactor.

In this series of experiments the use of MAO as the aluminum source and as the Lewis acid was tested. In aliphatic hydrocarbon solvents, no isolated polymer (even at extended reaction time of 4 hours) was obtained and the experiments were unsuccessful. This failure was likely due to the insolubility of MAO in cyclohexane.

In toluene, the mixture of Nd{C(SiHMe$_2$)$_3$}$_3$ and MAO provided a moderately active site that reacted primarily by 1,4-trans-insertion. Addition of Ph$_3$CCl, either before adding MAO or after adding MAO, gave a highly active cis-selective site. This may be noted from Experiments 698 and 708: the order of addition for MAO and Ph$_3$CCl doesn't effect the cis:trans ratio and had no noticeable effect on the reactivity of the amount of polymer that can be isolated. It was noticed that the use of a commonly used organic chlorine donor (n-chlorosuccinimide) can influence the cis:trans ratio but it had to be used with a borane source.

Similarly high activity and high selectivity was obtained with simply alkylaluminum reagents, chloride source, and Nd{C(SiHMe$_2$)$_3$}$_3$ (Table 3).

TABLE 3

Nd{C(SiHMe$_2$)$_3$}$_3$ + _ + _ → 3 charges of BD at 60° C. reacted for 60 minutes

| RXN# | Precatalyst Conditions | Vinyl:Trans:Cis | General Reactivity |
|---|---|---|---|
| 728 | [Nd] + 100 TIBA (Cyclohexane) | Needed | Moderate |
| 719 | [Nd] + 2 Ph$_3$CCl + 100 TIBA (Cyclohexane) | 5:20:75 | High |
| 721 | [Nd] + 2 [$^i$Pr$_2$EtNH][Cl] + 100 TIBA (cyclohexane) | 4:12:84 | High |
| 722 | [Nd] + 2 [nBu$_3$NH][Cl] + 100 TIBA (cyclohexane) | Needed | High |

In this series of experiments, the effect of variations in the chlorine donors was explored. Remarkably, ammonium chlorides were effective activators as long as a bulky amine was the byproduct of the protonolysis. Two ammonium chlorides known to have no or very small interactions with anything other than a proton were tested. In NMR experiments with La{C(SiHMe$_2$)$_3$}$_3$ and these ammonium chlorides, HC(SiHMe$_2$)$_3$ and free amine were produced as byproducts. This suggested that protonolysis of the alkyl ligands was an effective approach to activate the precatalysts. No metal species from reactions with Ph$_3$CCl nor ammonium chlorides were isolated. When used for polymerization under the set reaction parameters listed above, it was found that DIPEA-Cl gave a polymer with higher cis selectivity than Ph$_3$CCl.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A precatalyst having the structure of Formula (I):

wherein
M is a lanthanide or a transition metal; and
Alk is $C_{1-6}$ alkyl,
wherein the lanthanide metal is selected from the group consisting of La, Ce, Pr, Nd, Pm, Sm, Eu, Gd, Tb, Dy, Ho, Er, Tm, and Yb; and
wherein the transition metal is selected from the group consisting of Sc, Ti, V, Cr, Mn, Fe, Co, Ni, Cu, Y, Zr, Nb, Mo, Tc, Ru, Rh, Pd, Ag, Cd, La, Hf, Ta, W, Re, Os, Ir, Pt, Au, Hg, Ac, Rf, and Ha; and
wherein if Alk is Me, then M is not Y, La, Ce, or Pr.

2. The precatalyst according to claim 1, wherein M is Sc, Y, La, Ce, Pr, Nd, Pm, Sm, Eu, Gd, Tb, Dy, Ho, Er, Tm, or Yb.

3. The precatalyst according to claim 1, wherein M is Nd.

4. The precatalyst according to claim 1, wherein the precatalyst has the structure of Formula (Ia):

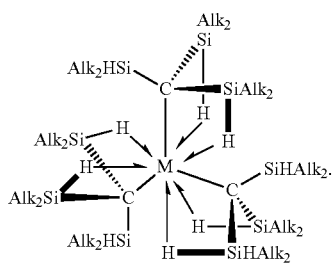

5. The precatalyst according to claim 1, wherein the precatalyst has the structure of Formula (Ib):

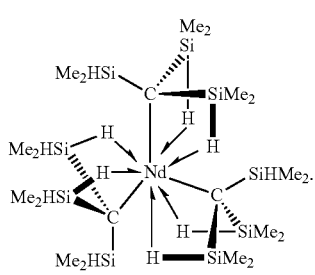

6. A catalyst comprising the structure of Formula (II):

wherein
M is a lanthanide or a transition metal;
Alk is $C_{1-6}$ alkyl;
X is halide, bis(oxazolinato), carboxylate, acetyl acetonate, amidate, alkoxide, amide, $BR_4$, $AlR_4$, or alkyl aluminoxane;
R is independently selected at each occurrence thereof from the group consisting of H, $C_6F_5$, phenyl, and $C_{1-6}$ alkyl;
wherein the lanthanide metal is selected from the group consisting of La, Ce, Pr, Nd, Pm, Sm, Eu, Gd, Tb, Dy, Ho, Er, Tm, and Yb; and
wherein the transition metal is selected from the group consisting of Sc, Ti, V, Cr, Mn, Fe, Co, Ni, Cu, Y, Zr, Nb, Mo, Tc, Ru, Rh, Pd, Ag, Cd, La, Hf, Ta, W, Re, Os, Ir, Pt, Au, Hg, Ac, Rf, and Ha; and
wherein if Alk is Me, then M is not Y, La, Ce, or Pr.

7. The precatalyst according to claim 6, wherein M is Sc, Y, La, Ce, Pr, Nd, Pm, Sm, Eu, Gd, Tb, Dy, Ho, Er, Tm, or Yb.

8. The catalyst according to claim 6, wherein M is Nd.

9. The catalyst according to claim 6, wherein X is F, Cl, Br, I, $O_2CR^1$, methylaluminoxane (MAO), or $[Ph_3C][B(C_6F_5)_4]$, and wherein $R^1$ is $C_{1-12}$ alkyl.

10. The catalyst according to claim 6, wherein the catalyst comprises the structure of Formula (IIa):

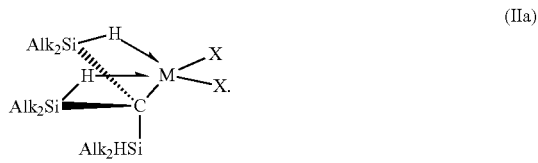

11. The catalyst according to claim 6, wherein the catalyst comprises the structure of Formula (IIb):

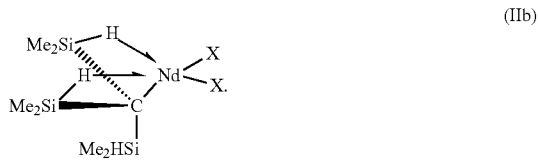

12. A catalyst according to claim 6, wherein the catalyst having the structure of Formula (II) is supported by an inert carrier.

13. The catalyst according to claim 12, wherein the inert carrier is a porous solid selected from the group consisting of talc, a sheet silicate, an inorganic oxide, and a finely divided polymer powder.

14. A process for preparation of a catalyst comprising:
providing a precatalyst having the structure of Formula (I):

wherein
M is a lanthanide or a transition metal; and
Alk is $C_{1-6}$ alkyl;
wherein the lanthanide metal is selected from the group consisting of La, Ce, Pr, Nd, Pm, Sm, Eu, Gd, Tb, Dy, Ho, Er, Tm, and Yb; and
wherein the transition metal is selected from the group consisting of Sc, Ti, V, Cr, Mn, Fe, Co, Ni, Cu, Y, Zr, Nb, Mo, Tc, Ru, Rh, Pd, Ag, Cd, La, Hf, Ta, W, Re, Os, Ir, Pt, Au, Hg, Ac, Rf, and Ha;
wherein if Alk is Me, then M is not Y, La, Ce, or Pr;
providing a Lewis acid or a halide source; and
forming the catalyst by reacting the precatalyst having the structure of Formula (I) with the Lewis acid or the halide source.

15. The precatalyst according to claim 14, wherein M is Sc, Y, La, Ce, Pr, Nd, Pm, Sm, Eu, Gd, Tb, Dy, Ho, Er, Tm, or Yb.

16. The process according to claim 14, wherein M is Nd.

17. The process according to claim 14, wherein the catalyst is formed with a Lewis acid, said Lewis acid being selected from the group consisting of $[Ph_3C][B(C_6F_5)_4]$, $B(C_6F_5)_3$, $Ph_3B$, $PhB(C_6H_5)_2$, methylaluminoxane (MAO), modified methylaluminoxane (MMAO), ethylaluminoxane, propylaluminoxane, isopropylaluminoxane, butylaluminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentylaluminoxane, phenylaluminoxane, 2,6-dimethylphenylaluminoxane, ethylaluminum sesquichloride, diisobutylaluminum chloride, diethylaluminum chloride, ethylaluminum dichloride, ethylaluminum sesquichloride, isobutylaluminum dichloride, dimethylaluminum chloride, isobutylaluminum dichloride, diethylaluminum iodide, diethylaluminum chloride, diisopropylaluminum chloride, diisobutylaluminum chloride, dioctylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenylbutylaluminum chloride, phenylisobutylaluminum chloride, phenyloctylaluminum chloride, p-tolylethylaluminum chloride, p-tolylpropylaluminum chloride, p-tolylisopropylaluminum chloride, p-tolylbutylaluminum chloride, p-tolylisobutylaluminum chloride, p-tolyloctylaluminum chloride, benzylethylaluminum chloride, benzylpropylaluminum chloride, benzylisopropylaluminum chloride, benzylbutylaluminum chloride, benzylisobutylaluminum chloride, benzyloctylaluminum chloride, propylaluminum dichloride, isopropylaluminum dichloride, butylaluminum dichloride, isobutylaluminum dichloride, and octylaluminum dichloride.

18. The process according to claim 14, wherein the catalyst is formed with a halide source, said halide source being $Ph_3C$-Hal, N-chlorosuccinimide, $[Alk_3NH][Hal]$, or an electrophilic chlorine source, wherein Hal is halogen and each Alk is independently selected in each occurrence thereof from $C_{1-6}$ alkyl.

19. The process according to claim 14, wherein said providing a precatalyst comprises:
    providing a first intermediate compound having the structure of Formula (III):

$$MI_3THF_n \quad (III),$$

wherein n is 1 to 9; and
    reacting the first intermediate compound with a compound having the structure of Formula (IV):

$$M_1C(SiHAlk_2)_3 \quad (IV),$$

wherein
    $M_1$ is a metal;
    under conditions effective to produce the precatalyst.

20. The process according to claim 19, wherein $M_1$ is K and Alk is Me.

21. A catalyst prepared by the process according to claim 14.

22. A catalyst according to claim 21, wherein the catalyst is supported by an inert carrier.

23. The catalyst according to claim 22, wherein the inert carrier is a porous solid selected from the group consisting of talc, a sheet silicate, an inorganic oxide, and a finely divided polymer powder.

24. The process according to claim 14, wherein the catalyst comprises a structure of Formula (II):

$$MC(SiHAlk_2)_3X_2 \quad (II),$$

wherein
X is halide, bis(oxazolinato), carboxylate, acetyl acetonate, amidate, alkoxide, amide, $BR_4$, $AlR_4$, or alkyl aluminoxane; and
R is independently selected at each occurrence thereof from the group consisting of H, $C_6F_5$, phenyl, and $C_{1-6}$ alkyl.

25. The process according to claim 24, wherein X is F, Cl, Br, I, $O_2CR^1$, methylaluminoxane (MAO), or $[Ph_3C][B(C_6F_5)_4]$, and wherein $R^1$ is $C_{1-12}$ alkyl.

26. The process according to claim 24, wherein the catalyst comprises the structure of Formula (IIa):

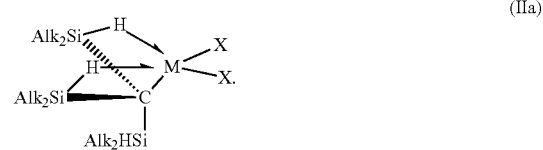

(IIa)

27. The process according to claim 24, wherein the catalyst comprises the structure of Formula (IIb):

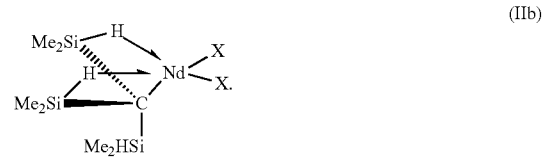

(IIb)

28. A process for preparation of a precatalyst having the structure of Formula (I):

$$M\{C(SiHAlk_2)_3\}_3$$

wherein
M is a lanthanide or a transition metal; and
Alk is $C_{1-6}$ alkyl;
wherein the lanthanide metal is selected from the group consisting of La, Ce, Pr, Nd, Pm, Sm, Eu, Gd, Tb, Dy, Ho, Er, Tm, and Yb; and
wherein the transition metal is selected from the group consisting of Sc, Ti, V, Cr, Mn, Fe, Co, Ni, Cu, Y, Zr, Nb, Mo, Tc, Ru, Rh, Pd, Ag, Cd, La, Hf, Ta, W, Re, Os, Ir, Pt, Au, Hg, Ac, Rf, and Ha;
wherein if Alk is Me, then M is not Y, La, Ce, or Pr;
said process comprising:
providing a first intermediate compound having the structure of Formula (III):

$$MI_3THF_n \quad (III),$$

wherein n is 1 to 9 and
forming the precatalyst from the first intermediate compound of Formula (III).

29. The process according to claim 28, wherein said forming the precatalyst comprises:
reacting the first intermediate compound with a compound having the structure of Formula (IV):

$$M_1C(SiHAlk_2)_3 \quad (IV),$$

wherein $M_1$ is a metal;
under conditions effective to produce the precatalyst.

30. The process according to claim 28, wherein $M_1$ is K and Alk is Me.

31. The process according to claim 28, wherein the precatalyst has the structure of Formula (Ia):

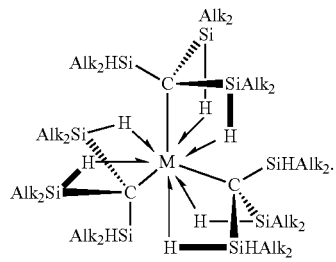

(Ia)

32. The process according to claim 28, wherein the precatalyst has the structure of Formula (Ib):

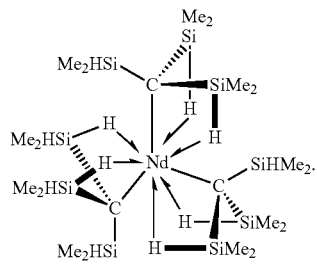

(Ib)

33. A process for polymerizing unsaturated hydrocarbon monomers, said process comprising:
  providing unsaturated hydrocarbon monomers;
  providing a catalyst comprising the structure of Formula (II):

$$MC(SiHAlk_2)_3X_2 \qquad (II),$$

wherein
  M is a lanthanide or a transition metal;
  Alk is $C_{1-6}$ alkyl;
  X is halide, bis(oxazolinato), carboxylate, acetyl acetonate, amidate, alkoxide, amide, $BR_4$, $AlR_4$, or alkyl aluminoxane;
  R is independently selected at each occurrence thereof from the group consisting of H, $C_6F_5$, phenyl, and $C_{1-6}$ alkyl; and
  wherein if Alk is Me, then M is not Y, La, Ce, or Pr; and
  polymerizing the unsaturated hydrocarbon monomers in the presence of the catalyst under conditions effective to produce a polymer.

34. The process according to claim 33, wherein M is a rare earth metal.

35. The process according to claim 33, wherein M is Nd.

36. The process according to claim 33, wherein X is F, Cl, Br, I, $O_2CR^1$, methylaluminoxane (MAO), or $[Ph_3C][B(C_6F_5)_4]$, and wherein $R^1$ is $C_{1-12}$ alkyl.

37. The process according to claim 33, wherein the catalyst comprises the structure of Formula (IIa):

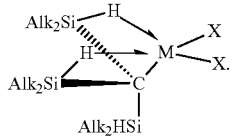

(IIa)

38. The process according to claim 33, wherein the catalyst comprises the structure of Formula (IIb):

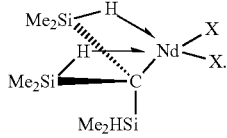

(IIb)

39. The process according to claim 33, wherein the unsaturated hydrocarbon monomer is diene, styrene or ethylene.

40. The process according to claim 39, wherein diene is 1,3-butadiene or isoprene.

41. The process according to claim 33, wherein the polymer is polybutadiene or polyisoprene.

42. The process according to claim 33, wherein polymerization is carried out in a presence of a solvent.

43. The process according to claim 42, wherein the solvent is a non-polar solvent.

44. The process according to claim 43, wherein the non-polar solvent is cyclohexane, hexane, heptane, or toluene.

45. A process for polymerizing unsaturated hydrocarbon monomers, said process comprising:
  providing unsaturated hydrocarbon monomers;
  providing a catalyst, wherein the catalyst is prepared by the process comprising:
    providing a precatalyst having the structure of Formula (I):

$$M\{C(SiHAlk_2)_3\}_3 \qquad (I),$$

wherein
    M is a lanthanide or a transition metal; and
    Alk is $C_{1-6}$ alkyl;
    wherein if Alk is Me, then M is not Y, La, Ce, or Pr;
  reacting the precatalyst of Formula (I) under conditions effective to produce the catalyst; and
  polymerizing the unsaturated hydrocarbon monomers in the presence of the catalyst under conditions effective to produce polymer.

46. The process according to claim 45, wherein M is a rare earth metal.

47. The process according to claim 45, wherein M is Nd.

48. The process according to claim 45, wherein said reacting comprises:
  reacting the precatalyst with a Lewis acid and/or an alkylaluminum reagent under conditions effective to produce the catalyst.

49. The process according to claim 45, wherein said reacting comprises:
  reacting the precatalyst with an alkylaluminum reagent and/or a halide source under conditions effective to produce the catalyst.

50. The process according to claim 45, wherein said reacting comprises:

reacting the precatalyst with a Lewis acid and/or a halide source under conditions effective to produce the catalyst.

51. The process according to claim 45, wherein the unsaturated hydrocarbon monomer is diene, styrene or ethylene.

52. The process according to claim 51, wherein diene is 1,3-butadiene or isoprene.

53. The process according to claim 45, wherein the polymer is polybutadiene or polyisoprene.

54. The process according to claim 45, wherein polymerization is carried in a presence of a solvent.

55. The process according to claim 54, wherein the solvent is a non-polar solvent.

56. The process according to claim 55, wherein the non-polar solvent is cyclohexane, hexane, heptane, or toluene.

57. The process according to claim 48, wherein the precatalyst is reacted with an alkylaluminum reagent, said alkylaluminum reagent being selected from the group consisting of triisobutylaluminium (TIBA), methylaluminoxane (MAO), modified methylaluminoxane (MMAO), ethylaluminoxane, propylaluminoxane, isopropylaluminoxane, butylaluminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentylaluminoxane, phenylaluminoxane, 2,6-dimethylphenylaluminoxane, trimethylaluminum, tripropylaluminum, trihexylaluminum, trioctylaluminum, triethylaluminum, triisoprenylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, ethyldibenzylaluminum, triisopropylaluminum, tributylaluminum, tripentylaluminum, diazobythylaluminum hydride, diethylaluminum hydride, diisopropylaluminum hydride, dibutylaluminum hydride, diisobutylaluminum hydride, dioctylaluminumhydride, diphenylaluminum hydride, di-p-tolylaluminum hydride, dibenzylaluminum hydride, phenylethylaluminum hydride, phenylpropylaluminum hydride, phenylisopropylaluminum hydride, phenylbutylaluminum hydride, phenylisobutylaluminum hydride, phenyloctylaluminum hydride, p-tolylethylaluminum hydride, p-tolylpropylaluminum hydride, p-tolylisopropylaluminum hydride, p-tolylbutylaluminum hydride, p-tolylisobutylaluminum hydride, p-tolyloctylaluminum hydride, benzylethylaluminum hydride, benzylpropylaluminum hydride, benzylisopropylaluminum hydride, benzylbutylaluminum hydride, benzylisobutylaluminum hydride, and benzyloctylaluminum hydride.

58. The process according to claim 49, wherein the precatalyst is reacted with an alkylaluminum reagent, said alkylaluminum reagent being selected from the group consisting of triisobutylaluminium (TIBA), methylaluminoxane (MAO), modified methylaluminoxane (MMAO), ethylaluminoxane, propylaluminoxane, isopropylaluminoxane, butylaluminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentylaluminoxane, phenylaluminoxane, 2,6-dimethylphenylaluminoxane, trimethylaluminum, tripropylaluminum, trihexylaluminum, trioctylaluminum, triethylaluminum, triisoprenylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, ethyldibenzylaluminum, triisopropylaluminum, tributylaluminum, tripentylaluminum, diazobythylaluminum hydride, diethylaluminum hydride, diisopropylaluminum hydride, dibutylaluminum hydride, diisobutylaluminum hydride, dioctylaluminumhydride, diphenylaluminum hydride, di-p-tolylaluminum hydride, dibenzylaluminum hydride, phenylethylaluminum hydride, phenylpropylaluminum hydride, phenylisopropylaluminum hydride, phenylbutylaluminum hydride, phenylisobutylaluminum hydride, phenyloctylaluminum hydride, p-tolylethylaluminum hydride, p-tolylpropylaluminum hydride, p-tolylisopropylaluminum hydride, p-tolylbutylaluminum hydride, p-tolylisobutylaluminum hydride, p-tolyloctylaluminum hydride, benzylethylaluminum hydride, benzylpropylaluminum hydride, benzylisopropylaluminum hydride, benzylbutylaluminum hydride, benzylisobutylaluminum hydride, and benzyloctylaluminum hydride.

59. The process according to claim 48, wherein the precatalyst is reacted with a Lewis acid, said Lewis acid being selected from the group consisting of [$Ph_3C$][B($C_6F_5$)$_4$], B($C_6F_5$)$_3$, $Ph_3B$, PhB($C_6H_5$)$_2$, $Ph_3CCl$, methylaluminoxane (MAO), modified methylaluminoxane (MMAO), ethylaluminoxane, propylaluminoxane, isopropylaluminoxane, butylauminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentylaluminoxane, phenylaluminoxane, 2,6-dimethylphenylaluminoxane, ethylaluminum sesquichloride, diisobutylaluminum chloride, diethylaluminum chloride, ethylaluminum dichloride, ethylaluminum sesquichloride, isobutylaluminum dichloride, dimethylaluminum chloride, isobutylaluminum dichloride, diethylaluminum iodide, diethylaluminum chloride, diisopropylaluminum chloride, diisobutylaluminum chloride, dioctylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenylbutylaluminum chloride, phenylisobutylaluminum chloride, phenyloctylaluminum chloride, p-tolylethylaluminum chloride, p-tolylpropylaluminum chloride, p-tolylisopropylaluminum chloride, p-tolylbutylaluminum chloride, p-tolylisobutylaluminum chloride, p-tolyloctylaluminum chloride, benzylethylaluminum chloride, benzylpropylaluminum chloride, benzylisopropylaluminum chloride, benzylbutylaluminum chloride, benzylisobutylaluminum chloride, benzyloctylaluminum chloride, propylaluminum dichloride, isopropylaluminum dichloride, butylaluminum dichloride, isobutylaluminum dichloride, and octylaluminum dichloride.

60. The process according to claim 50, wherein the precatalyst is reacted with a Lewis acid, said Lewis acid being selected from the group consisting of [$Ph_3C$][B($C_6F_5$)$_4$], B($C_6F_5$)$_3$, $Ph_3B$, PhB($C_6H_5$)$_2$, $Ph_3CCl$, methylaluminoxane (MAO), modified methylaluminoxane (MMAO), ethylaluminoxane, propylaluminoxane, isopropylaluminoxane, butylauminoxane, isobutylaluminoxane, pentylaluminoxane, neopentylaluminoxane, hexylaluminoxane, octylaluminoxane, 2-ethylhexylaluminoxane, cyclohexylaluminoxane, 1-methylcyclopentylaluminoxane, phenylaluminoxane, 2,6-dimethylphenylaluminoxane, ethylaluminum sesquichloride, diisobutylaluminum chloride, diethylaluminum chloride, ethylaluminum dichloride, ethylaluminum sesquichloride, isobutylaluminum dichloride, dimethylaluminum chloride, isobutylaluminum dichloride, diethylaluminum iodide, diethylaluminum chloride, diisopropylaluminum chloride, diisobutylaluminum chloride, dioctylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenylbutylaluminum chloride, phenylisobutylaluminum chloride, phenyloctylaluminum chloride, p-tolylethylaluminum chloride, p-tolylpropylaluminum chloride, p-tolylisopropylaluminum chloride, p-tolylbutylaluminum chloride, p-tolylisobutylaluminum chloride, p-tolyloctylaluminum chloride, benzylethylaluminum chloride, benzylpropylaluminum chloride, benzylisopropylaluminum chloride, benzylbutylaluminum chloride, benzylisobutylaluminum chloride, benzyloctylaluminum chloride, propylaluminum dichloride, isopropylaluminum dichloride, butylaluminum dichloride, isobutylaluminum dichloride, and octylaluminum dichloride.

61. The process according to claim 49, wherein the precatalyst is reacted with a halide source, said halide source being $Ph_3C$-Hal, N-chlorosuccinimide, $[Alk_3NH][Hal]$, or an electrophilic chlorine source, wherein Hal is halogen and each Alk is independently selected in each occurrence thereof from $C_{1-6}$ alkyl.

62. The process according to claim 50, wherein the precatalyst is reacted with a halide source, said halide source being $Ph_3C$-Hal, N-chlorosuccinimide, $[Alk_3NH][Hal]$, or an electrophilic chlorine source, wherein Hal is halogen and each Alk is independently selected in each occurrence thereof from $C_{1-6}$ alkyl.

* * * * *